United States Patent
Murakoshi

(10) Patent No.: US 7,785,472 B2
(45) Date of Patent: Aug. 31, 2010

(54) CARBON NANOTUBE STRUCTURE-SELECTIVE SEPARATION AND SURFACE FIXATION

(75) Inventor: Kei Murakoshi, Hokkaido (JP)

(73) Assignee: Japan Science and Technology Agency, Saitama (JP)

( * ) Notice: Subject to any disclaimer, the term of this patent is extended or adjusted under 35 U.S.C. 154(b) by 688 days.

(21) Appl. No.: 10/597,790

(22) PCT Filed: Feb. 10, 2005

(86) PCT No.: PCT/JP2005/002085

§ 371 (c)(1),
(2), (4) Date: Jul. 27, 2007

(87) PCT Pub. No.: WO2005/077827

PCT Pub. Date: Aug. 25, 2005

(65) Prior Publication Data

US 2007/0258880 A1 Nov. 8, 2007

(30) Foreign Application Priority Data

Feb. 16, 2004 (JP) .............................. 2004-039100

(51) Int. Cl.
*B01D 15/08* (2006.01)
*C09C 1/44* (2006.01)
(52) U.S. Cl. ................ 210/656; 209/1; 209/3; 209/4; 210/695; 210/748.01; 210/749; 423/460; 423/461; 977/745; 977/748; 977/751; 977/845; 977/848
(58) Field of Classification Search .............. 210/656, 210/695, 748, 749, 806; 423/460, 461; 977/745, 977/748, 751, 845, 848; 209/1, 3, 4
See application file for complete search history.

(56) References Cited

U.S. PATENT DOCUMENTS 7,074,310 B2 * 7/2006 Smalley et al. .............. 204/450

(Continued)

FOREIGN PATENT DOCUMENTS

CA 2477299 10/2003

(Continued)

OTHER PUBLICATIONS

Zheng, Ming, et al., Structure-Based Carbon Nanotube Sorting by Sequence-Dependent DNA Assembly, Science, 2003, vol. 302, No. 5650, p. 1545-1548.

(Continued)

*Primary Examiner*—Joseph W Drodge
(74) *Attorney, Agent, or Firm*—Snell & Wilmer L.L.P.

(57) ABSTRACT

A method of separating, concentrating or purifying uniform carbon nanotubes with desired properties (diameter, chiral vector, etc) in a highly sensitive manner by the use of structure-sensitive properties peculiar to carbon nanotubes; and an apparatus therefor. There is provided a method of separating, concentrating, or purifying carbon nanotubes with the desired properties contained in a sample, comprising the steps of (a) irradiating a sample containing carbon nanotubes with light; and (b) selecting carbon nanotubes with desired properties. In a preferred embodiment, the light irradiation of the step (a) can be carried out in the presence of a metal so as to cause specified carbon nanotubes to selectively induce a photocatalytic reaction, resulting in metal deposition. Further, in a preferred embodiment, a given magnetic filed can be applied in the steps (b) so as to attain accumulation or concentration or carbon nanotubes with metal deposited.

15 Claims, 12 Drawing Sheets

U.S. PATENT DOCUMENTS

| | | | |
|---|---|---|---|
| 7,131,537 B2 * | 11/2006 | Papadimitrakopoulos | 209/18 |
| 7,374,685 B2 * | 5/2008 | Sun | 210/639 |
| 7,481,990 B2 * | 1/2009 | Wong et al. | 423/460 |
| 7,572,426 B2 * | 8/2009 | Strano et al. | 423/447.1 |

FOREIGN PATENT DOCUMENTS

| | | |
|---|---|---|
| CN | 1405083 | 3/2003 |
| EP | 1284236 | 2/2003 |
| EP | 1591417 | 11/2008 |
| JP | 08/231210 | 9/1996 |
| JP | 2003-095626 | 4/2003 |
| JP | 2003-128406 | 5/2003 |
| JP | 2003-171107 | 6/2003 |
| WO | WO 2004/060801 | 7/2004 |

OTHER PUBLICATIONS

Dodziuk, Helena, et al., Water solubilization, determination of the number of different types of single-wall carbon nanotubes and their partial separation with respect to diameters by complexation with n-cyclodextrin, Chem. Comm., 2003, No. 8, p. 986-987.

Chattopadhyay, et al., A Route for Bulk Separation of Semiconducting from Metallic Single-Wall Carbon Nanotubes, J. Am. Chem. Soc., 2003, vol. 125, No. 11, p. 3370-3375.

Krupke, Ralph, Separation of Metallic from Semiconducting Single-Walled Carbon Nanotubes, Science, 2003, vol. 301, No. 5631, p. 344-347.

Yudasaka, M., et al., Diameter-selective removal of single-wall carbon nanotubes through light-assisted oxidation, Chemical Physics Letters, 2003, vol. 374, p. 132-136.

Umek, P., et al., Separation of SWNTs by diffusion, Synthetic Metals, 2001, vol. 121, p. 1211-1212.

International Search Report dated May 31, 2005.

Chinese Office Action dated Jun. 13, 2008.

Braidy, N., et al. "Oxidation of Fe Nanoparticles Embedded in Single-Walled Carbon Nanotubes by Exposure to a Bright Flash of White Light," Nano Letters, ACS, Washington DC US, vol. 2, No. 11, Jan. 1, 2002, pp. 1277-1280.

Supplemental European Search Report issued in corresponding European Application No, 05710137.0 dated Mar. 3, 2010.

Canadian Office Action from corresponding Application No. 2,556,562 dated March 5, 2010.

* cited by examiner

CARBON NANOTUBE STRUCTURE-SELECTIVE SEPARATION AND SURFACE FIXATION

TECHNICAL FIELD

The present invention relates to a method and an apparatus for highly selectively separating, concentrating, and refining carbon nanotubes (CNTs). The invention also relates to a high purity carbon nanotube separated by the method of the invention, and a thin film and an array thereof. The invention further provides an optical device or an electronic device using the carbon nanotube film.

BACKGROUND ART

A carbon nanotube is a new substance discovered by Sumio Iijima in 1991, which can exhibit a metallic and/or semiconducting property depending on the diameter thereof and the way the tube is wound. The individual physical property of the carbon nanotube is entirely different depending on the structure of the tube, and study within the art is currently being vigorously undertaken. In addition, the carbon nanotube is a substance, of which much is expected as a next generation material for use in devices and the like, having applications in the field of electronics and energy.

From studies on a process for producing a single-walled carbon nanotube (SWNT), an industrially low-cost mass-production of the carbon nanotube (the Chemical Vapor Deposition or CVD method) has nearly been established, for example, by decomposition of a hydrocarbon using ferrocene as a catalyst (see, for example, Non-Patent Document 1). As such, the carbon nanotube has been commercialized. As a representative example of a method for synthesizing a single-walled carbon nanotube, there are an arc discharge method and a laser evaporation method (e.g., see Non-Patent Document 2). The carbon nanotube is further purified by ultrafiltration (e.g., see Non-Patent Document 2), wherein a purity of 90% or more is obtainable.

The distribution of the diameters of single-walled carbon nanotubes produced by an arc discharge differs depending on the type of metal catalyst to be used in the synthesis. In this way, it is possible to control the average diameter of the carbon nanotube by selecting the type of metal catalyst, and thereby the distribution of the diameter of the carbon nanotube produced can be controlled with an average diameter in the range of ±0.4 nm. However, any method among the existing production methods does not allow a selective synthesis of a single-walled carbon nanotube which has a particular diameter.

Therefore, studies for establishing a method for the separation and purification of certain carbon nanotubes from carbon nanotubes given by the above-mentioned existing production method, have been carried out in order to investigate the characteristic physical properties of said individual carbon nanotubes separated and purified.

For an example, P. Umek and D. Mihailovic carried out agarose gel electrophoresis of single-walled carbon nanotubes dispersed in aqueous sodium dodecyl sulfate (SDS) solution, followed by hydrochloric acid treatment, removal of SDS using deionized water, desiccation, and Raman spectroscopy examination of the resultant respective fractions. This confirmed that the single-walled carbon nanotubes were partially separated on the basis of diameter and length thereof (see, e.g., Non-Patent Document 3).

Further, Stephen K. Doom et al. carried out capillary electrophoresis of a solution of carbon nanotubes dispersed in SDS and found, from absorption spectra and Raman spectra of respective separated carbon nanotubes, that the single-walled carbon nanotubes could be separated depending on differences in the elution time among respective carbon nanotubes, which reflects the difference in the length thereof. (see, e.g., Non-Patent Document 4). The above-mentioned studies have nearly established a method for separating the carbon nanotube based on the length thereof.

However, the characteristic physical property of the carbon nanotube is determined depending on a multiple physical properties such as the diameter and the chiral angle thereof, which means that separation of carbon nanotubes based only on the length thereof does not necessarily correspond to the separation based on the characteristic physical property thereof. Therefore, to date, the length-based separations of carbon nanotubes is not sufficient to define the characteristic physical property thereof.

Although many studies have been performed so far on carbon nanotubes, the precision has still remained very low for the preparation, separation or purification of single-walled tubes which have the same diameter, chirality, work function, and band gap (see, e.g., Non-Patent Documents 5 to 12). With respect to the resultant separation based on diameter, Non-Patent Document 9, which discloses a separation of DNA-CNT by ion exchange chromatography, is an example of a related prior art. However, it is completely different in the principle from the present invention, and inferior to the technique of the present invention in separation precision. Further, there are some patent applications directed to a method for purification of a carbon nanotube (see, e.g., Patent Documents 1 to 5). However, all of these Patent Documents 1 to 5 only disclose techniques of impurity removal. Thus these documents do not describe any separation of carbon nanotubes which have a uniform characteristic physical property, wherein diameter, chiral angle and the like thereof, are respectively the same.

Although various studies have contributed to the characterization of the electron structure of carbon nanotubes, which are dependent on the structures of respective carbon nanotubes, very limited information is available on the absolute potential in the energy level of the carbon nanotube, with the widespread impression that while a monomolecular carbon nanotube has various structures, the absolute potential of the Fermi level of individual carbon nanotubes is considered to be at a similar level. By investigating spectral features of Raman scattering (especially in the radial breathing mode ($w=150-240$ $cm^{-1}$)) of isolated single-walled carbon nanotubes (SWNT) which are metallic or semiconducting in solution under a potential control, we are the first in the world to have discovered that the Fermi level of tubes was found to positively shift greatly with the decrease of tube diameters. These observations suggest that the work function of the tube depends heavily upon the structure of the SWNT. Further, we also have discovered that the structural dependence of a metallic carbon nanotube is significantly larger than that of a semiconducting carbon nanotube. The great difference in the work function means that, for example, a carbon nanotube with a specific diameter is more stable than a noble metal (e.g., Au and Pt), and that on the other hand, a carbon nanotube with a larger diameter has the same degree of tendency to release electrons as Mg and Al. Based on the above discussions, it has first been made clear that the characteristic physical properties of a single carbon nanotube has a significant dependence upon the diameter, chirality thereof, and the like.

In order to put carbon nanotubes, which are expected to be the next generation material, into practical utilization, it is inevitably required to control the physical properties dominated by the diameter and chirality thereof, and the like.

Therefore, an innovative separation method has to be established to sort the carbon nanotube in accordance with the desired physical properties to be utilized.

Patent Document 1: Japanese Patent Application Laid-Open No. 8-198611
Patent Document 2: JAPANESE PATENT APPLICATION LAID-OPEN No. 2003-81616
Patent Document 3: JAPANESE PATENT APPLICATION LAID-OPEN No. 2003-300714
Patent Document 4: JAPANESE PATENT APPLICATION LAID-OPEN No. 2003-212526
Patent Document 5: JAPANESE PATENT APPLICATION LAID-OPEN No. 2002-515847
Non-Patent Document 1: Kazuyoshi Tanaka, Challenge to Carbon Nanotube Device, Kagaku Dojin (2001)
Non-Patent Document 2: Yahachi Saito and Shunji bando, Basis of Carbon Nanotube, Corona (1998)
Non-Patent Document 3: P. Umek and Mihailovic, Synthetic Metals, 121, 1211-1212 (2001)
Non-Patent Document 4: Stephen K. Doom, Robert E. Fields, III, Hui, Hu, Mark A. Hamon, Robert C. Haddon, John P. Selegue, and Vahid Majidi, J. Am. Chem. Soc., 124, 3169-3174 (2002)
Non-Patent Document 5: R. Kfupke et al., Science, 301, 344-347 (2003)
Non-Patent Document 6: G. S. Duesberg et al., Chem. Comm., 435-436 (1998)
Non-Patent Document 7: G. S. Duesberg et al., Appl. Phys., A67, 117-119 (1998)
Non-Patent Document 8: D. Chattopadhyay et al., J. Am. Chem. Soc., 124 728-729 (2002)
Non-Patent Document 9: M. Zheng et al., Science, 302, 1545-1548 (2003)
Non-Patent Document 10: H. Dodziuk et al., Chem. Comm., 986-987 (2003)
Non-Patent Document 11: D. Chattopadhyay et al., J. Am. Chem. Soc., 125, 3370-3375 (2003)
Non-Patent Document 12: Z. H. Chen et al., Nano Lett., 1245-1249 (2003)

DISCLOSURE OF THE INVENTION

Problems to be Solved by the Invention

The present invention takes advantage of the correlation between the structure-sensitive electronic energy level of a carbon nanotube and the redox potential of a metal, in order to obtain carbon nanotubes which have a desired physical property. The present inventive process comprises providing different metal ions, which have different respective redox potentials, as well as carbon nanotubes which have different respective electronic energy levels, wherein the energy levels are sensitive to diameter, chirality or the like thereof; and causing a redox reaction between the metal ions and the carbon nanotubes, which have an energy band gap enabling the absorption of near-infrared light in a magnetic field, through excitation by light irradiation to deposit the metals on the surface of the carbon nanotube, thereby precipitating only the desired carbon nanotube.

The object of the invention is to provide a method and an apparatus for highly selectively separating, concentrating or refining carbon nanotubes which have desired physical properties, especially uniformity in at least either a diameter or a chiral vector, by utilizing the structure-sensitive particular property of the carbon nanotubes.

Another object of the invention is to apply, as a next generation material in electronics and energy fields, a thin film of high purity carbon nanotubes separated by the above-mentioned method to optical or electronic devices.

Means for Solving the Problems

The present invention provides the following:

(1) A method of separating, concentrating, or refining a carbon nanotube having a desired physical property from a sample, comprising steps of:
a) irradiating light to a sample containing carbon nanotubes and
b) selecting the carbon nanotubes having the desired physical property.

(2) The method according to item (1), wherein said physical property includes at least either a diameter or a chiral vector.

(3) The method according to item (1), wherein said carbon nanotube has a single-walled structure.

(4) The method according to item (1), wherein said light has a certain wavelength within a range covering from the near infrared region to the ultraviolet region.

(5) The method according to item (4), wherein said light is monochromatic light or laser light having said wavelength.

(6) The method according to item (1), wherein light irradiation in the step a) is carried out in the presence of metal ions.

(7) The method according to item (6), wherein said metal ion is selected from the group consisting of alkali metals; alkaline earth metals; transition metals selected from the group consisting of Group IIIA to Group VIIA elements, Group VIII elements, and Group IB elements; and rare earth elements.

(8) The method according to item (1), wherein the step b) is carried out by applying a predetermined magnetic field to said carbon nanotube so as to precipitate the carbon nanotube with the desired physical property.

(9) The method according to item (1), wherein the step b) is carried out by chromatography.

(10) The method according to item (1), wherein said sample further contains a surfactant.

(11) The method according to item (10), wherein said surfactant is selected from the group consisting of sodium dodecyl sulfate, sodium dodecylbenzenesulfonate, Triton X, alkylsulfonates, sodium polyoxyethylene alkyl ether sulfate, benzalconium chloride, alkyltrimethylammonium chloride, benzyltrimethylammonium chloride, nonyl phenol ethoxylate, octyl phenyl polyoxyethylene ether, lauryl polyoxyethylene ether, and cetyl polyoxyethylene ether.

(12) The method according to item (1), wherein said sample is a water-based dispersion or an aqueous solution of the carbon nanotubes.

(13) The method according to item (1), wherein said carbon nanotubes are surface modified with a saturated or unsaturated carbon chain molecule having a carboxyl group or an amino group as a substituent in the molecule through a covalent bond, an ionic bond, a hydrogen bond, or an intermolecular interaction.

(14) The method according to item (1), wherein said sample is a solution further containing a metal ion and an electron donor.

(15) The method according to item (14), wherein said solution contains the metal ion at a concentration of 0.001 to 10%.

(16) The method according to item (14), wherein said solution contains the electron donor at a concentration of 0.001 to 10%.

(17) The method according to item (14), wherein said electron donor is selected from the group consisting of alcohols, amines, arginine, benzaldehyde, hydrazine, carboxylic acids, amino acids, toluene, alkylbenzenes, terpenes, ethers, silanes, and thiols.

(18) A method for analyzing a carbon nanotube having a desired physical property in a sample, comprising the following steps of:
a) irradiating light to the sample expected to contain the carbon nanotube;
b) selecting the carbon nanotube having the desired physical property; and
c) identifying the selected carbon nanotube.

(19) The method according item (18), wherein said physical property includes at least either a diameter or a chiral vector.

(20) A carbon nanotube separated by the method according to item (2), having uniformity in at least either a diameter or a chiral vector.

(21) A carbon nanotube composition, obtained by the method according to item (2), wherein the composition has an increased content of the carbon nanotube having uniformity in at least either a diameter or a chiral vector.

(22) A carbon nanotube composition containing a carbon nanotube having uniformity in at least either a diameter or a chiral vector with greater than or equal to 99% purity.

(23) A carbon nanotube thin film obtained by adsorbing and fixing the carbon nanotube according to item (20) on a support.

(24) A carbon nanotube array obtained by adsorbing and fixing the carbon nanotube according to item (20) arranged in predefined patterns on a support.

(25) An optical filter comprising the carbon nanotube thin film according to item (23).

(26) An electronic device comprising the carbon nanotube thin film according to item (23).

(27) The electronic device according to item (26), selected from the group consisting of a conductive thin film, a dielectric thin film, a sensor electrode, an electrode for a high energy density fuel cell, a highly functional display, a single-molecule detection sensor, an acceleration detection sensor, and a magnetic field detection sensor.

(28) An apparatus for separating, concentrating, or refining a carbon nanotube having a desired physical property in a sample, comprising
A) an introduction part for a sample containing the carbon nanotubes;
B) means for irradiating light to the sample; and
C) means for selecting the carbon nanotube having the desired physical property.

(29) The apparatus according to item (28), wherein said physical property includes at least either a diameter or a chiral vector.

(30) The apparatus according to item (28), wherein said means B) is a light source of monochromatic light or laser light having a certain wavelength within a range covering from the near infrared region to the ultraviolet region.

(31) The apparatus according to item (28), wherein said means B) is a polychromatic light source within a range covering from the near infrared region to the ultraviolet region for depositing a metal on the carbon nanotube.

(32) The apparatus according to item (28), wherein said means C) is an electromagnet with controllable magnetism for generating a predetermined magnetic field for depositing the carbon nanotube having the desired physical property.

(33) The apparatus according to item (28), wherein said means C) is chromatography.

(34) The apparatus according to item (28), wherein said sample is a solution further containing a surfactant.

(35) The apparatus according to item (28), wherein said sample is a water-based dispersion or an aqueous solution of the carbon nanotube.

(36) The apparatus according to item (28), wherein said sample is a solution further containing a metal ion and an electron donor.

EFFECT OF THE INVENTION

The present method and/or apparatus described herein can provide highly selective separation, concentration or purification of carbon nanotubes having a uniform physical property, especially at least either a diameter or a chiral vector, by taking advantage of the structure-sensitive properties of carbon nanotubes.

BEST MODES OF THE EMBODIMENTS OF THE INVENTION

Figure 1A:
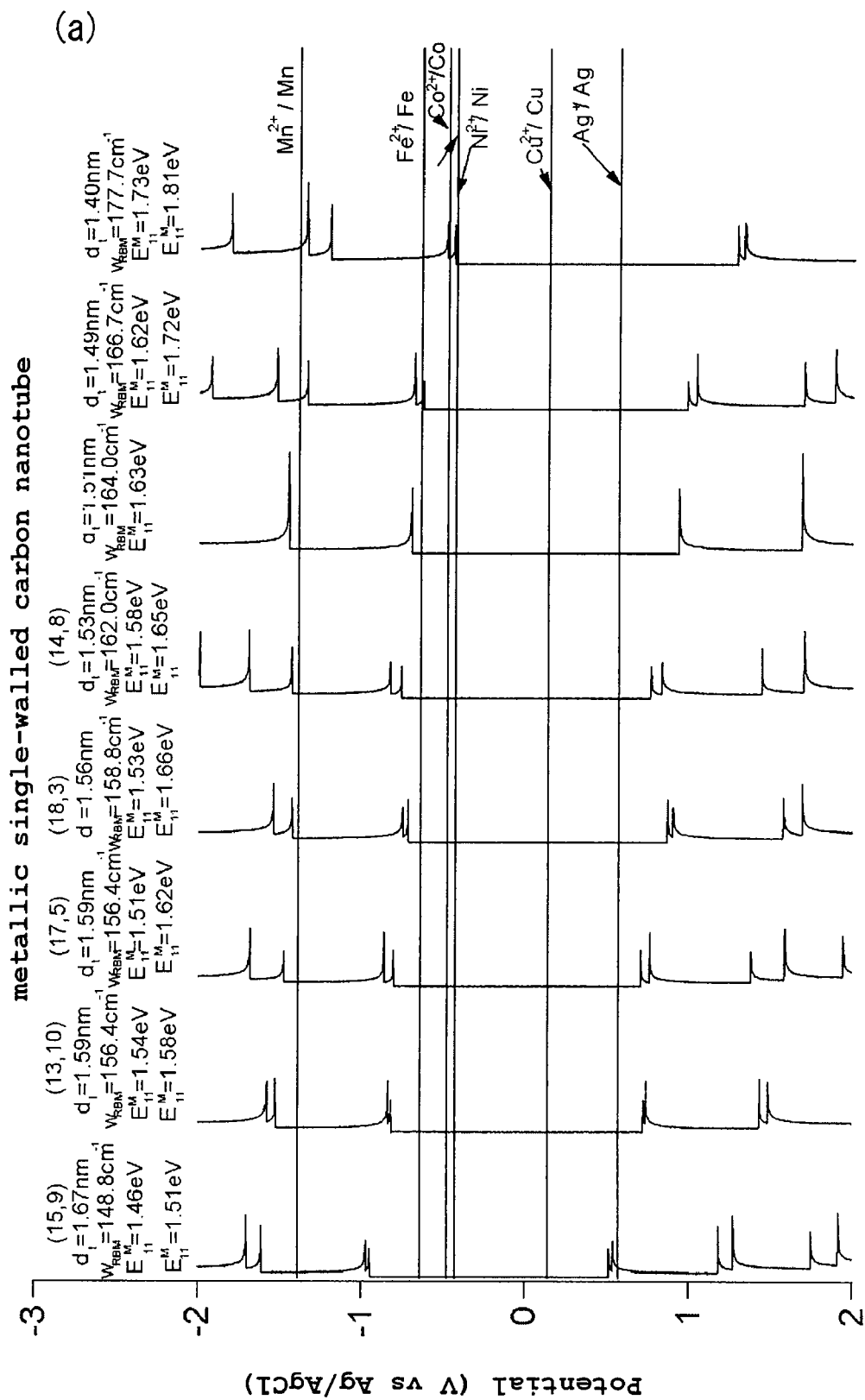
FIG. 1A shows a correlation between an electronic energy level of a carbon nanotube and a redox potential of a metal in the case of (a), a metallic single-walled carbon nanotube.

Hereinafter, the present invention will be described. It should be understood that, throughout the specification, expressions in singular forms also include concepts of plural forms unless otherwise stated. Furthermore, it should be understood that the terms as used herein have the meanings which are generally referred to in the field, unless otherwise stated.

Terms

Hereinafter, definitions of the terms used herein will be listed.

As used herein, "carbon nanotube (Carbon NanoTube, abbreviation: CNT)" refers to a type of carbon cluster represented as $C_n$ (n is an integer, indicting number of carbon atoms), which is a structure comprising a single layer or multiple layers of graphite rolled up to form a cylindrical shape. The structure of the carbon nanotube is defined in accordance with the physical properties such as diameter, chiral vector thereof and the like, wherein the chiral vector defines a degree of twist, and the way of winding such as rightward-winding, leftward-winding and the like. The representative examples of the structures include, but are not limited to, (5,5) armchair type, (9,0) zigzag type, (9, 1) chiral type, and the like. The "carbon nanotube" according to the invention may be a "single-walled carbon nanotube (abbreviation: SWNT)", which comprises a one-atom-thick layer of graphite, or a "multi-walled carbon nanotube (abbreviation: MWNT)", which comprises multiple layers of graphite rolled in on themselves to form a tube shape.

The "carbon nanotube" of the invention may also be a pure carbon nanotube or a carbon nanotube substituted with any proper substituent for enabling solvation of the carbon nanotube to a water-based or organic solvent. In one preferable embodiment, the "carbon nanotube" of the invention may be surface-modified with a saturated or unsaturated carbon chain molecule having a carboxyl group or an amino group as a substituent in the molecule through a covalent bond, an ionic bond, a hydrogen bond, or intermolecular interaction.

The "carbon nanotube" of the invention can be produced by the following three conventional methods.

A) Arc Discharge Method

The arc discharge method is a method employed for manufacturing a carbon nanotube in the early period. Two graphite rod electrodes are arranged as closely as several nanometers to each other, and then applied, in an atmosphere of an inert gas, with high voltage provided by the DC power source connected to the electrodes so as to volatilize the graphite rods through the resultant high intensity discharge between the cathode and anode, thereby forming carbon clusters. Cooling of the obtained carbon clusters up to room temperature deposits them on the cathode in various forms such as carbon nanotube, fullerene and the like. While only multi-walled carbon nanotubes may form in the absence of a catalyst, single-walled carbon nanotubes may form in the presence of some metal catalysts such as Co, Ni or Fe.

B) Laser Evaporation Method

Similar to the above-mentioned method, graphite rods are used in the method. Specifically, for example, Nd/YAG laser irradiation evaporates graphite rods with argon gas which flows slowly at 500 Torri in an electric furnace, heading up to approximately 1200, thereby forming SWNTs. The method allows for a large-scale production of SWNTs.

C) Chemical Vapor Deposition Method (CVD Method)

In this CVD method, for example, the substrate is exposed to volatile precursors such as methane, which at high temperature (e.g., 600° C.) can be a source of atoms, and decompose on the substrate surface to release carbon atoms, thereby forming carbon nanotubes though configuration of bonds. Although the CVD method is more suitable for industrial mass production as compared with the above-mentioned two methods, the CVD method is not suitable for production of a single-walled carbon nanotube.

Carbon nanotubes which are commercially available may be subjected to the purification and separation process according to the present invention.

As used herein, "sample containing carbon nanotube(s)" may include the carbon nanotubes produced by the above-mentioned three methods, carbon nanotubes which are commercially available, and crude compositions which are expected to contain carbon nanotubes; as well as organic solutions, aqueous solutions or water-based dispersions containing the crude compositions. The above mentioned "sample containing carbon nanotube(s)" can further contain impurities such as a surfactant and an electron donor. In addition to the produced carbon nanotubes, the above-mentioned crude compositions may contain metals or various carbon impurities.

As used herein, "selecting" or "selection (of)" a carbon nanotube having a desired physical property, refers to precipitating or concentrating an carbon nanotube of subject from a crude composition containing or expected to contain the carbon nanotube. "Selecting" may further include the step of separating the precipitated or concentrated material.

As used herein, "separating" or "separation (of)" a carbon nanotube with a desired physical property refers to substantially separating from a native environment, where the carbon nanotube exists in a sample before separation, or refining or purifying the carbon nanotube.

As used herein, "purifying", "purification", "refining" or "refinement" of a carbon nanotube with a desired physical property refers to removing at least one of components accompanied with the carbon nanotube in the native environment, where the carbon nanotube exists in a sample. Therefore, the scope intended in a practical form of these terms partially overlaps with the scope of "separation". Although the state of the purified carbon nanotube indicates higher density of the carbon nanotubes than that of the corresponding unpurified state, which means the nanotube is in a concentrated state, the concept of "purification" also comprises the state where the carbon nanotubes are not concentrated, but has at least one of the components which is accompanied in native state, removed out.

As used herein, "concentrating" or "concentration" of a carbon nanotube with a desired physical property refers to a process for increasing the content of a substance of interest in a sample as compared to the corresponding content of the substance in the unconsecrated state. Accordingly, the concept of "concentration" overlaps with those of "purification" and/or "separation". Although the concentrated substance (e.g., a carbon nanotube with a desired physical property) remains in a sample with a decreased content of an impurity as compared to that of the impurity in an unconcentrated state, there may be an increased content of another certain impurity in the concentrated state, indicating that the concept of "concentrated" state comprises a state which is not "purified".

As used herein, "identifying" or "identification" refers to determination of characteristics of a subject substance. There are various measuring methods for identification, which include, but not limited to, physical analysis methods such as Raman spectroscopy.

As used herein, "physical property" or "physical properties" refers to a physical character of carbon nanotube, including, for example, diameter, chiral vector, length and the like.

As used herein, "single-walled structure" refers to a structure comprising a single layer of graphite rolled up to form a cylindrical shape of a carbon nanotube. Raman spectroscopy can estimate whether or not a carbon nanotube has a single-walled structure. The resonance Raman effects in the case of SWNT allows detection of single isolated tubes. A strong signal can be observed in a region of which Raman shift is equal to or less than 400 $cm^{-1}$ of the Raman spectrum, wherein the region is called radial breathing mode. The frequency of the radial breathing mode is commonly known as being proportional to the inverse of the nanotube diameter. Therefore, by performing Raman spectrum measurement, it is possible to confirm the existence of the single-walled carbon nanotube and to determine the diameter of the carbon nanotube. In addition, in the case of the multi-walled carbon nanotube, it is known that although the observation of MWNT with a transmission electron microscope (TEM) can confirm its tube-like shape, the signal is very weak in the radial breathing mode in the Raman spectrum measurement.

As used herein, "magnetic field" refers to a field being in a physical state on which a magnetic force works. The field can be found in the vicinity of a magnet or a medium in which electric current flows. As used herein, means for providing the magnetic field in the invention includes, but not limited to, a permanent magnet or an electromagnet which can control magnetism.

As used herein, "chromatography" refers to one of the methods for separating a specific targeted substance or substance group in a sample of a mixture from other substances which coexist in the sample, wherein the method involves utilizing the difference in mobility (equilibrium distribution) among the substances which travel in a carrier (stationary phase). Therefore, any technique which can separate a targeted substance in a sample form other components of the sample, falls within the scope of "chromatography". The chromatography may be employed for separating a desired substance from a mixture or for qualitatively or quantitatively analyzing the desired substance. For example, as used herein, an electrophoresis technique, which is usually not called chromatography, falls within the scope of the chromatography, since the electrophoresis technique can separate at least one components in a sample of a mixture from the other components of the sample. The stationary phase is generally a liquid or a solid. The mobile phase is generally a liquid or a gas. By adsorbing a sample on one of the ends of a stationary phase such as an adsorbent or a mobile phase; and running a proper solvent, which comprises the mobile phase together with the sample, on or through the stationary phase, the components in the sample travels through the stationary phase while repeatedly making adsorption with, or elution from, a certain portion of the stationary phase such as the surface or the inside of the stationary phase. During the travel of the components, the difference in mobility among the components allows for the separation of the mixture, wherein the mobility of respective components reflects the degree of preference in adsorbing with the stationary phase. The technique which uses a liquid as the mobile phase, is called liquid chromatography. Conventionally, depending on whether the mobile phase is a liquid or a gas, the chromatography is classified into liquid chromatography (LLC and LSC, HPLC and FPLC (trade name)) and gas chromatography (e.g. GLC, GSC). Also, the separation mechanism categorizes chromatography techniques, for example, as chiral chromatography, adsorption chromatography, distribution chromatography, ion exchange chromatography, hydrophobic chromatography, size-excluding chromatography (gel chromatography such as gel permeation chromatography (GPC) and gel filtration chromatography (GFC)), salting-out chromatography, reversed phase chromatography, affinity chromatography, supercritical fluid chromatography, high performance counter flow distribution chromatography, and perfusion chromatography. Also, depending on the form of the solid phase, chromatography can be classified into, for example, column chromatography, thin layer chromatography (e.g. paper chromatography) and the like. The method of the invention can employ any type of the above mentioned chromatographic techniques.

As used herein, "electron donor" refers to a compound which donates electrons to the occupied energy level of the carbon nanotube which have loose electrons. Examples of the electron donor of the invention include, but are not limited to, alcohols, amines, arginine, benzaldehyde, hydrazine, carboxylic acids, amino acids, toluene, alkylbenzenes, terpenes, ethers, silanes, and thiols. These exemplary electron donors are as defined below. A preferable donor in the invention is methanol.

As used herein, "support" and "substrate" are interchangeably used unless otherwise specified, and refer to a material which is preferably a solid, and is capable of supporting another substance in the presence of a fluid (particularly, a solvent such as a liquid). The material for the support may include, but are not limited to, any solid materials which have a property to be bonded with a substance of the invention by a covalent bond or a non-covalent bond or have been modified into a derivative so as to have such a property. The support may be maintained, more preferably, in a solid state under conditions for purification, concentration, separation, or analysis. The material to be used as the support may be any material which can form solid surfaces, including, but not limited to, for example, glass (e.g., slide glass), silica, silicon, ceramics, silicon dioxide, plastics, metals (including alloys), natural and synthetic polymers (e.g., polystyrene, cellulose, chitosan, dextran, and nylon). The support may be composed of multiple layers of different materials. For example, as the support, there are used a plurality of inorganic insulating materials, including, for example, but not limited to glass, quartz glass, alumina, sapphire, forsterite, silicon carbide, silicon oxide, silicon nitride, and the like. Further, examples of the material used as the support may include, but are not limited to, organic materials such as polyethylene, ethylene, polypropylene, polyisobutylene, polyethylene terephthalate, unsaturated polyester, fluorine-containing resin, polyvinyl chloride, polyvinylidene chloride, polyvinyl acetate, polyvinyl alcohol, polyvinyl acetal, acrylic resin, polyacrylonitrile, polystyrene, acetal resin, polycarbonate, polyamide, phenol resin, urea resin, epoxy resin, melamine resin, styrene-acrylonitrile copolymer, acrylonitrile-butadiene-styrene copolymer, silicone resin, polyphenylene oxide, polysulfone and the like. Films used for blotting such as a nylon film, a nitrocellulose film, a PVDE film and the like can also be used in the present invention. In the case that a nylon film is used, the results can be analyzed using a simple analysis system. In the case of analysis of a specimen with a high density, it is preferable to use a harder material such as glass.

As used herein for carbon nanotubes in the present invention, "adsorption/fixation" refers to physical or chemical adsorption on a "support" or "substrate". For the physical adsorption, a technique may be employed for spreading carbon nanotubes on a plane to form a film. The morphology of the film formed by spreading into a plane may include, for example, but are not limited to, a cast film, a monomolecular film, and a self-adsorption monomolecular film. As used herein, "cast film" refers to a film formed by casting method and such a cast film can be produced by casting a solution containing a material of the carbon nanotube and drying the cast solution. As used herein, "monomolecular film" refers to a film comprising a monomolecular layer of a thickness of nanometer order, formed at a gas-liquid interface or a solid-liquid interface. The invention will utilize a technique of transferring a monomolecular film containing the carbon nanotube of the invention onto a support. In the invention, it is preferable to employ a Langmuir-Blodgett film (so-called, LB film) among the "monomolecular film" as defined in a board sense, which are obtained through deposition from the surface of a solution containing a monolayer of the inventive carbon nanotubes onto a solid substrate by any method for transferring the monolayer onto the substrate. The most common methods for assembling a monomolecular film include, but are not limited to, a technique for dipping a solid support (or solid substrate) vertically, up and down in a monomolecular film on the surface of liquid under a controlled constant surface pressure. Another method for assembling monomolecular film includes a horizontal-lifting method, which can transfer only a single layer of monomolecular film onto a solid support. The horizontal-lifting method is a useful technique for the present invention.

As used herein, "accumulate" or "accumulation" refers to transferring a monomolecular film to a solid support, and the number of times of transferring the monomolecular film to the solid support may be one or more times. In order to accumulate monomolecular films on the solid support in the state where the films can retain their structure and organization as film, those skilled in the art can take various measures to produce the film while kept in the above state, but are required, at least, to spread the inventive carbon nanotubes on the surface of a liquid, thereby forming monomolecular films. Carbon nanotubes which consist of pure carbon can float in the water due to the hydrophobic property, and the carbon nanotubes may be used with or without substitution with hydrophilic functional group, wherein the hydrophilic functional group can render an amphiphilic property to the carbon nanotubes. As used herein, "self-adsorbing monomolecular film" refers to a monomolecular layer obtained by spontaneous chemical adsorption of the carbon nanotube molecule through a disulfide or dithiol on an evaporated metal substrate, such as an evaporated gold substrate.

As used herein, "introducing" or "introduction (of)" a sample refers to transferring a sample to a place where the reaction according to the invention will occur. A sample introduction part may have any shape as long as the shape is suitable for introducing a sample. Also, an example of methods for introducing a sample includes, but is not limited to, an injector method, an on-column method, a method of flowing the injected sample into a column by a mobile phase, a sample valve method and like. Means for introducing the sample may include, but not limited to, a sample injector, an auto-sampler, a micro-feeder and the like.

THEORY OF THE INVENTION

Figure 1B:
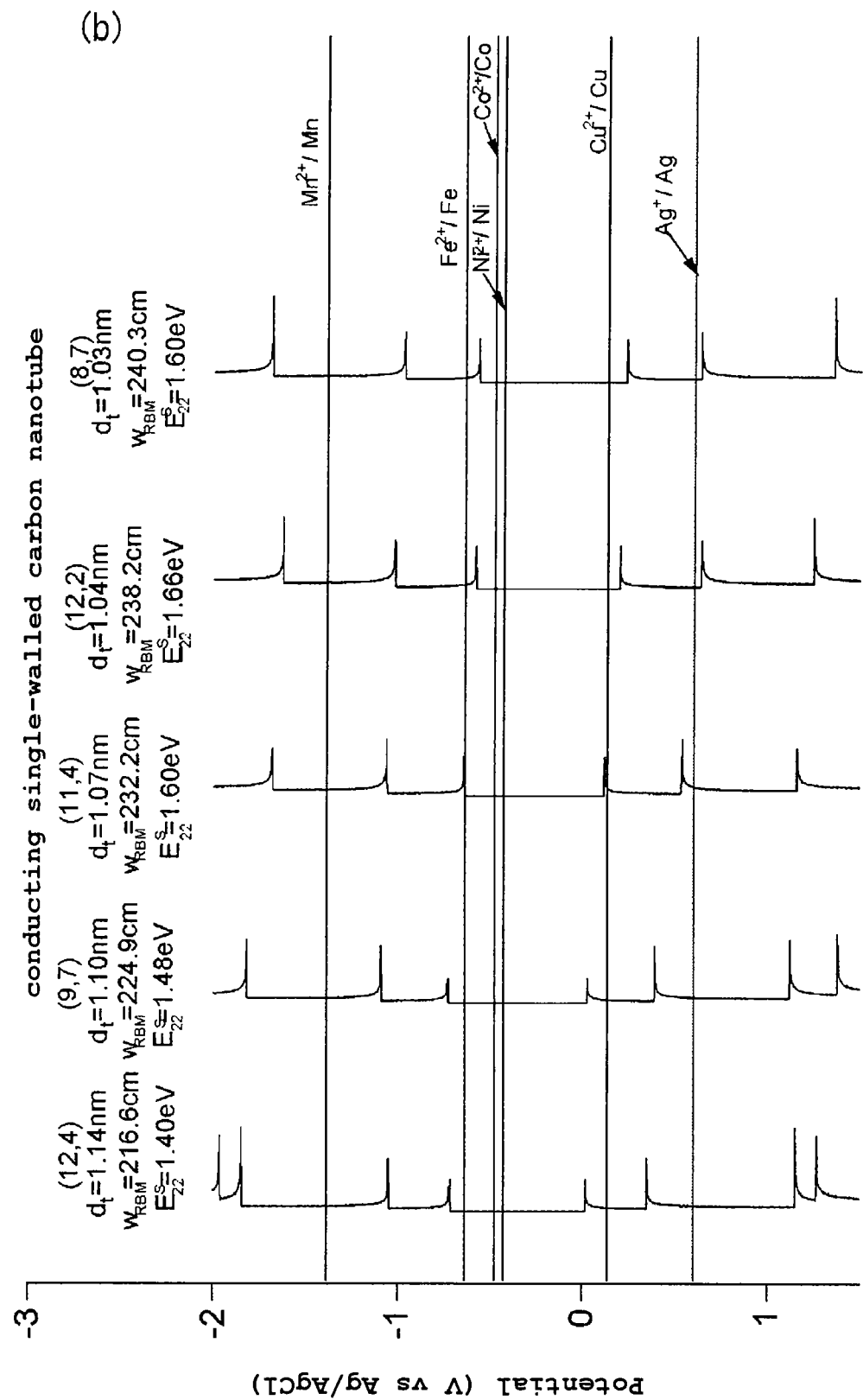
FIG. 1B shows a correlation between an electronic energy level of a carbon nanotube and a redox potential of a metal in the case of (b), a semiconducting single-walled carbon nanotube.

The theory of the invention is directed to a selective separation of carbon nanotubes for respective physical properties by taking advantage of the electronic energy level of a carbon nanotube and a redox potential of a metal. Here, the correlation between them is illustrated in FIG. 1.

Figure 2:
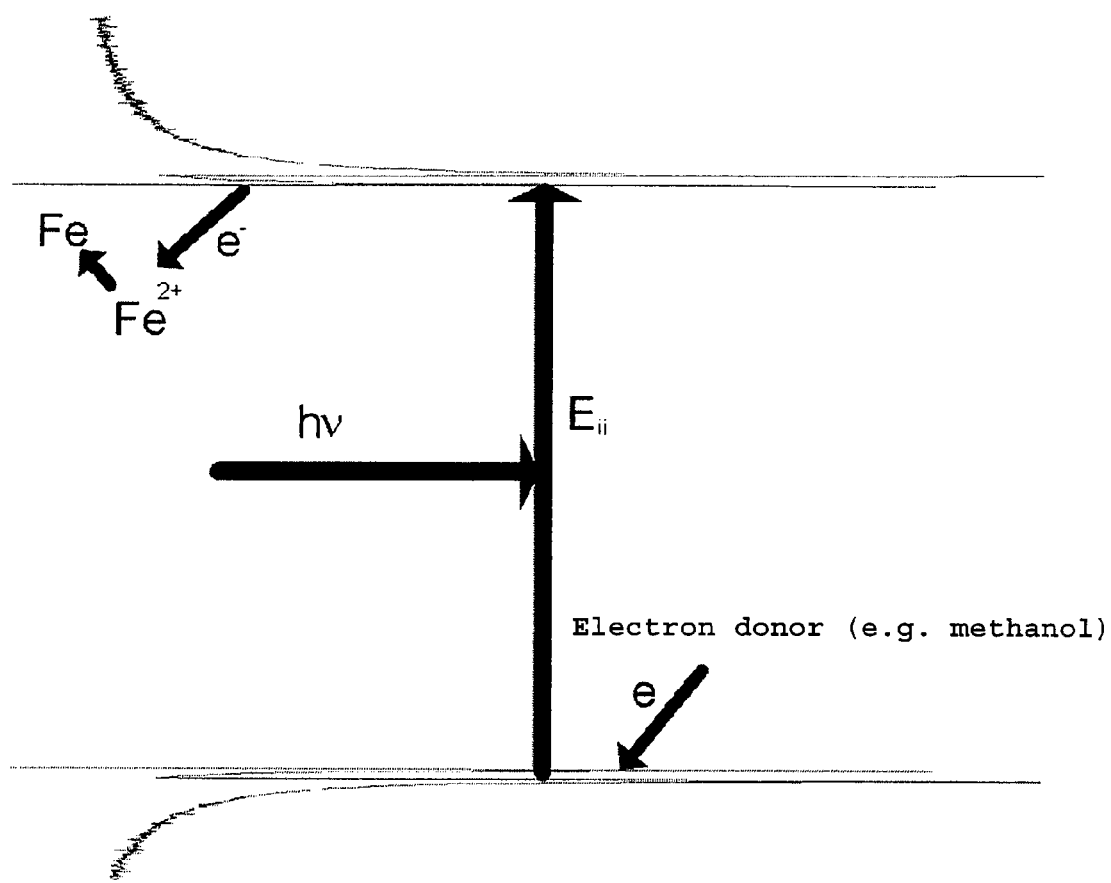
FIG. 2 shows a reaction mechanism expected between a single-walled carbon nanotube and a metal ion in the invention.

A possible reaction mechanism between a carbon nanotube and a metal ion, expected in view of the above correlation, is illustrated in FIG. 2. That is, FIG. 2 shows a possible reaction mechanism of $Fe^{2+}$ and a carbon nanotube, at an electronic energy level. For a detailed description of the mechanism, firstly, light irradiation will induce an electron transition in a carbon nanotube from an occupied level to a non-occupied level of the carbon nanotube, across the band gap of the tube, of which the magnitude corresponds to the excitation light energy. Then, the excited electron is transferred down to an energy level of a metal ion such as $Fe^{2+}$, since the non-occupied level is closer to the redox potential of the metal ion (in this case, $Fe^{2+}$) than the occupied level of the carbon nanotube. Consequently, $Fe^{2+}$ is converted into Fe and deposited on the carbon nanotube. The electron which has been lost from the occupied energy level of the carbon nanotube is compensated by supplying an electron to the occupied energy level of the carbon nanotube from methanol as an electron donor. That is the outline of the reaction mechanism expected in the invention.

Raman Spectroscopy of Carbon Nanotube

One embodiment of the invention is directed to a method of collecting carbon nanotubes which have uniformities in at least either of a diameter or a chiral vector, by reductive deposition of a metal on the carbon nanotubes through photocatalytic reaction, followed by application of a magnetic field so as to attract the deposited metal. The gathering behavior of the carbon nanotubes can be observed in a Raman spectrum.

Figure 3:
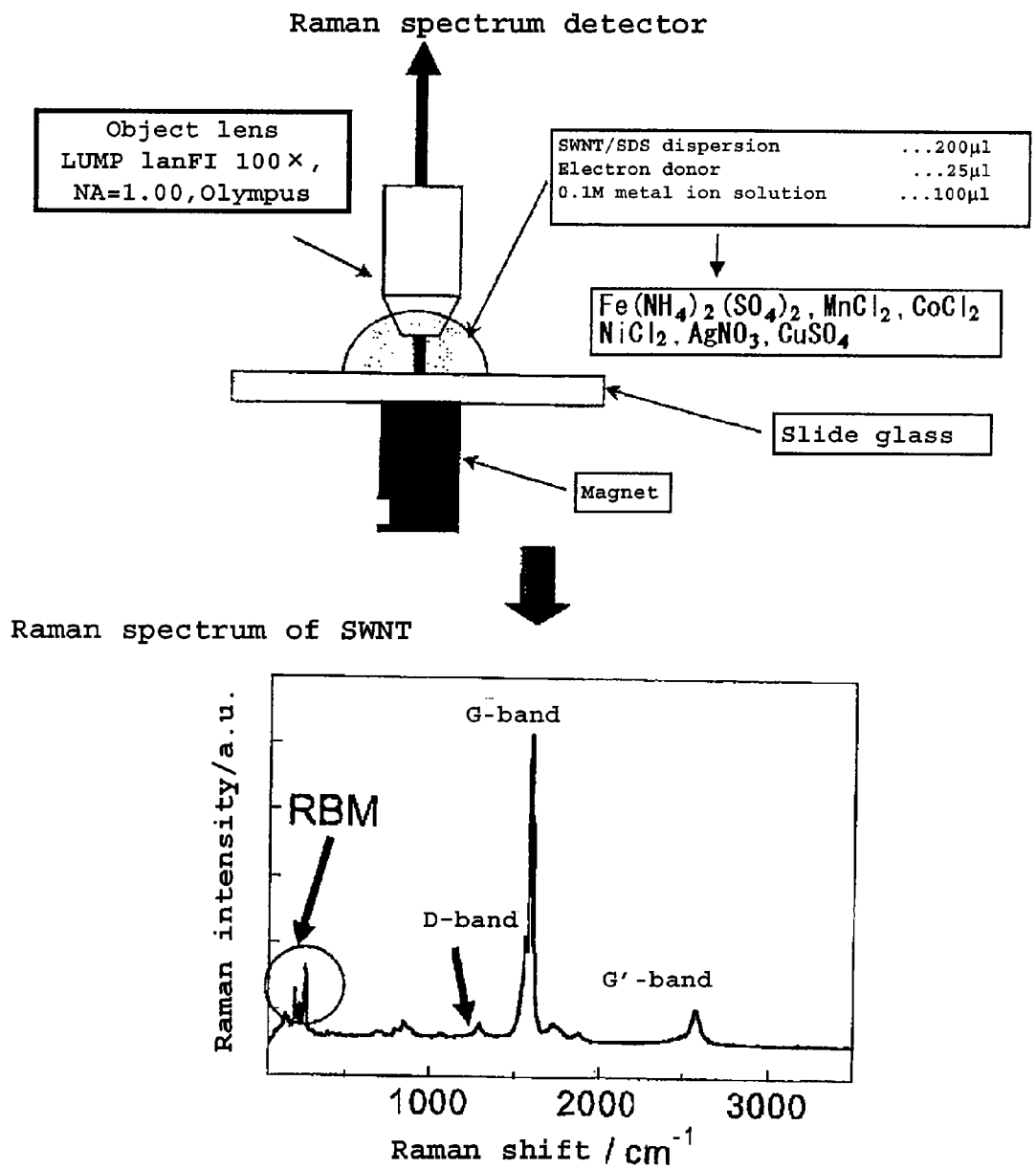
FIG. 3 shows schematic views of a Raman spectrum detector and a typical Raman spectrum of a single-walled carbon nanotube.

A Raman spectrum detector and a schematic drawing of a typical Raman spectrum of the carbon nanotube are shown in FIG. 3. The Raman spectrum of the carbon nanotube generally contains four kinds of modes (that is, RBM (Radial Breathing Mode), D-band, G-band, and G'-band). In the invention, by taking particular note of the RBM peak which depends on the diameter of the carbon nanotubes, the gathering behavior and selectivity of the carbon nanotube have been investigated.

Organic Chemistry

Organic chemistry is described in, for example, Organic Chemistry, R. T. Morrison, R. N. Boyd 5th ed. (1987) and the like, relevant portions of which are incorporated herein as a reference.

In this specification, unless otherwise specified, "substitution" means substitution of one or two or more hydrogen atoms in an organic compound or a substituent with another atom or an atomic group. It is possible that one hydrogen atom is removed and substituted with a monovalent substituent, and also that two hydrogen atoms are removed and substituted with a divalent substituent.

In the case that the carbon nanotube of the invention is substituted with a substituent R, one or a plurality of R groups exist and in the case that a plurality of R groups exist, the respective groups may be independently selected from the group consisting of hydrogen, alkyl, substituted alkyl, cycloalkyl, substituted cycloalkyl, alkenyl, substituted alkenyl, cycloalkenyl, substituted cycloalkenyl, alkinyl, substituted alkinyl, alkoxy, substituted alkoxy, carbocyclic group, substituted carbocyclic group, heterocyclic group, substituted heterocyclic group, halogen, hydroxy, substituted hydroxy, thiol, substituted thiol, cyano, nitro, amino, substituted amino, carboxy, substituted carboxy, acyl, substituted acyl, thiocarboxy, substituted thiocarboxy, amido, substituted amido, substituted carbonyl, substituted thiocarbonyl, substituted sulfonyl, and substituted sulfinyl.

The substituent R for making the carbon nanotube of the invention soluble in a water-based solvent is preferably polar groups such as carboxyl group (or carboxy group) or amino group or saturated or unsaturated carbon chains having a polar group such as carboxyl group or amino group in the molecule. On the other hand, as the substituent R for making the carbon nanotube of the invention soluble in an organic solvent, those which are hydrophobic are preferable and examples include C1-C6 alkyl, C1-C5 alkyl, C1-C4 alkyl, C1-C3 alkyl, and C1-C2 alkyl.

As used herein, "heterocyclic (group)" refers to groups having cyclic structure containing carbon atoms as well as hetero atoms. The hetero atoms may be selected from the group consisting of O, S, and N and they may be same or different and one or more hetero atoms may be included. The heterocyclic group may be aromatic or non-aromatic and also monocyclic or polycyclic. The heterocyclic group may be substituted.

As used herein, "carbon chain" refers to alkyl, substituted alkyl, cycloalkyl, substituted cycloalkyl, alkenyl, substituted alkenyl, cycloalkenyl, and substituted cycloalkenyl.

As used herein, "alkyl" refers to a monovalent group generated when one hydrogen atom is lost from aliphatic hydrocarbon (alkane) such as methane, ethane, propane, and the like, and is represented by $C_nH_{2n+1}$— in general (herein, n is a positive integer). Alkyl may be a straight chain or a branched chain. As used herein, "substituted alkyl" refers to an alkyl having the Hydrogen atom (H) of an alkyl substituted by a substituent as defined below. Specific examples of such alkyls may be, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, C1-C11 alkyl or C1-C12 alkyl, C1-C2 substituted alkyl, C1-C3 substituted alkyl, C1-C4 substituted alkyl, C1-C5 substituted alkyl, C1-C6 substituted alkyl, C1-C7 substituted alkyl, C1-C8 substituted alkyl, C1-C9 substituted alkyl, C1-C10 substituted alkyl, C1-C11 substituted alkyl, or C1-C12 substituted alkyl. Herein, for example, C1-C10 alkyl denotes straight chain or branched alkyl having 1-10 carbon atoms, and examples may be methyl($CH_3$—), ethyl($C_2H_5$—), n-propyl ($CH_3CH_2CH_2$—), isopropyl (($CH_3)_2CH$—), n-butyl ($CH_3CH_2CH_2CH_2$—), n-pentyl ($CH_3CH_2CH_2CH_2CH_2$—), n-hexyl ($CH_3CH_2CH_2CH_2CH_2CH_2$—), n-heptyl ($CH_3CH_2CH_2CH_2CH_2CH_2CH_2$—), n-octyl ($CH_3CH_2CH_2CH_2CH_2CH_2CH_2CH_2$—), n-nonyl ($CH_3CH_2CH_2CH_2CH_2CH_2CH_2CH_2CH_2$—), n-decyl ($CH_3CH_2CH_2CH_2CH_2CH_2CH_2CH_2CH_2CH_2$—), —$C(CH_3)_2$ $CH_2CH_2CH(CH_3)_2$, —$CH_2CH(CH_3)_2$ and the like. Further, for example, C1-C10 substituted alkyl refers to C1-C10 alkyl having one or more hydrogen atoms substituted by substituents.

As used herein, "lower alkyl" refers to C1-C6 alkyl and preferably C1 alkyl or C2 alkyl.

As used herein, "cycloalkyl" refers to an alkyl having a cyclic structure. The term "substituted cycloalkyl" refers to a cycloalkyl having the H of the cycloalkyl substituted by a substituent defined below. Specific examples of cycloalkyls may be C3-C4 cycloalkyl, C3-C5 cycloalkyl, C3-C6 cycloalkyl, C3-C7 cycloalkyl, C3-C8 cycloalkyl, C3-C9 cycloalkyl, C3-C10 cycloalkyl, C3-C11 cycloalkyl, C3-C12 cycloalkyl, C3-C4 substituted cycloalkyl, C3-C5 substituted cycloalkyl, C3-C6 substituted cycloalkyl, C3-C7 substituted cycloalkyl, C3-C8 substituted cycloalkyl, C3-C9 substituted cycloalkyl, C3-C10 substituted cycloalkyl, C3-C11 substituted cycloalkyl or C3-C12 substituted cycloalkyl. For example, cycloalkyl may be cyclopropyl, cyclohexyl, or the like.

As used herein, "alkenyl" refers to a monovalent group generated when one hydrogen atom is lost from an aliphatic hydrocarbon having one double bond in a molecule, such as ethylene and propylene, and, in general, is represented by $C_nH_{2n-1}$— (herein, n is a positive integer of 2 or higher). The term "substituted alkenyl" refers to an alkenyl having the H of the alkenyl substituted by a substituent as defined below. Specific examples of alkenyls may be C2-C3 alkenyl, C2-C4 alkenyl, C2-C5 alkenyl, C2-C6 alkenyl, C2-C7 alkenyl, C2-C8 alkenyl, C2-C9 alkenyl, C2-C10 alkenyl, C2-C11 alkenyl or C2-C12 alkenyl, C2-C3 substituted alkenyl, C2-C4 substituted alkenyl, C2-C5 substituted alkenyl, C2-C6 substituted alkenyl, C2-C7 substituted alkenyl, C2-C8 substituted alkenyl, C2-C9 substituted alkenyl, C2-C10 substituted alkenyl, C2-C11 substituted alkenyl or C2-C12 substituted alkenyl. Herein, for example, C2-C10 alkenyl refers to a straight chain or branched alkenyl including 2-10 carbon atoms, and examples of alkenyls include vinyl ($CH_2$=CH—), allyl ($CH_2$=$CHCH_2$—), $CH_3CH$=CH— and the like. Further, for example, C2-C10 substituted alkenyl refers to C2-C10 alkenyl which has 1 or more hydrogen atoms substituted by substituents.

As used herein, "cycloalkenyl" refers to an alkenyl having a cyclic structure. The term "substituted cycloalkenyl" refers to a cycloalkenyl having the H of a cycloalkenyl substituted by a substituent as defined below. Specific examples of cycloalkenyl may be C3-C4 cycloalkenyl, C3-C5 cycloalkenyl, C3-C6 cycloalkenyl, C3-C7 cycloalkenyl, C3-C8 cycloalkenyl, C3-C9 cycloalkenyl, C3-C10 cycloalkenyl, C3-C11 cycloalkenyl, C3-C12 cycloalkenyl, C3-C4 substituted cycloalkenyl, C3-C5 substituted cycloalkenyl, C3-C6 substituted cycloalkenyl, C3-C7 substituted cycloalkenyl, C3-C8 substituted cycloalkenyl, C3-C9 substituted cycloalkenyl, C3-C10 substituted cycloalkenyl, C3-C11 substituted cycloalkenyl or C3-C12 substituted cycloalkenyl. For example, preferable examples of cycloalkenyl include 1-cyclopentenyl, 2-cyclohexenyl or the like.

As used herein, "alkynyl" refers to a monovalent group generated when one hydrogen atom is lost from an aliphatic hydrocarbon having one triple bond in a molecule, such as acetylene, and, in general, is represented by $C_nH_{2n-3}$— (herein, n is a positive integer of 2 or higher). The term "substituted alkynyl" refers to alkynyl having the H of the alkynyl substituted by a substituent as defined below. Specific examples of alkynyls may be C2-C3 alkynyl, C2-C4 alkynyl, C2-C5 alkynyl, C2-C6 alkynyl, C2-C7 alkynyl, C2-C8 alkynyl, C2-C9 alkynyl, C2-C10 alkynyl, C2-C11 alkynyl, C2-C12 alkynyl, C2-C3 substituted alkynyl, C2-C4 substituted alkynyl, C2-C5 substituted alkynyl, C2-C6 substituted alkynyl, C2-C7 substituted alkynyl, C2-C8 substituted alkynyl, C2-C9 substituted alkynyl, C2-C10 substituted alkynyl, C2-C11 substituted alkynyl or C2-C12 substituted alkynyl. Herein, for example, C2-C10 alkynyl refers to, for example, a straight chain or branched alkynyl including 2-10 carbon atoms, and examples of alkynyl may be ethynyl (CH≡C—), 1-propynyl ($CH_3C$≡C—) or the like. Further, for example, C2-C10 substituted alkynyl refers to C2-C10 alkynyl having 1 or more hydrogen atoms substituted by substituents.

As used herein, "alkoxy" refers to a monovalent group generated when a hydrogen atom of a hydroxy group of an alcohol is lost, and in general, is represented by $C_nH_{2n+1}O$— (herein, n is an integer of one or higher). The term "substituted alkoxy" refers to alkoxy having H of the alkoxy substituted by a substituent as defined below. Specific examples of alkoxys may be C1-C2 alkoxy, C1-C3 alkoxy, C1-C4 alkoxy, C1-C5 alkoxy, C1-C6 alkoxy, C1-C7 alkoxy, C1-C8 alkoxy, C1-C9 alkoxy, C1-C10 alkoxy, C1-C11 alkoxy, C1-C12 alkoxy, C1-C2 substituted alkoxy, C1-C3 substituted alkoxy, C1-C4 substituted alkoxy, C1-C5 substituted alkoxy, C1-C6 substituted alkoxy, C1-C7 substituted alkoxy, C1-C8 substituted alkoxy, C1-C9 substituted alkoxy, C1-C10 substituted alkoxy, C1-C11 substituted alkoxy or C1-C12 substituted alkoxy. Herein, for example, C1-C10 alkoxy refers to a straight chain or branched alkoxy including 1-10 carbon atoms, and examples of alkoxys may be methoxy ($CH_3O$—), ethoxy ($C_2H_5O$—), n-propoxy ($CH_3CH_2CH_2O$—), and the like.

As used herein, "carbocyclic group" refers to a group which includes a cyclic structure including only carbons, and which is a group other than the above-mentioned "cycloalkyl", "substituted cycloalkyl", "cycloalkenyl", and "substituted cycloalkenyl". A carbocyclic group may be aromatic or nonaromatic, and may be monocyclic or polycyclic. The term "substituted carbocyclic group" refers to a carbocyclic group having the H of the carbocyclic group substituted by a substituent as defined below. Specific examples of carbocyclic groups may be C3-C4 carbocyclic group, C3-C5 carbocyclic group, C3-C6 carbocyclic group, C3-C7 carbocyclic group, C3-C8 carbocyclic group, C3-C9 carbocyclic group, C3-C10 carbocyclic group, C3-C11 carbocyclic group, C3-C12 carbocyclic group, C3-C4 substituted carbocyclic group, C3-C5 substituted carbocyclic group, C3-C6 substituted carbocyclic group, C3-C7 substituted carbocyclic group, C3-C8 substituted carbocyclic group, C3-C9 substituted carbocyclic group, C3-C10 substituted carbocyclic group, C3-C11 substituted carbocyclic group, or C3-C12 substituted carbocyclic group. The carbocyclic group may also be C4-C7 carbocyclic group or C4-C7 substituted carbocyclic group. The examples of carbocyclic group may be a phenyl group having one hydrogen atom deleted. The deletion site of the hydrogen may be any site which is chemically possible, and it may be on an aromatic ring or on a nonaromatic ring.

As used herein, "heterocyclic group" refers to a group having a cyclic structure including carbon and hetero atoms. Herein, hetero atoms may be selected from a group consisting of O, S and N, may be the same or different from each other, and one or more heteroatoms may be included. A heterocyclic group may be aromatic or nonaromatic, and may be monocyclic or polycyclic. The term "substituted heterocyclic group" refers to a heterocyclic group having the H of the heterocyclic group substituted by a substituent as defined below. Specific examples of heterocyclic group may be C3-C4 carbocyclic group, C3-C5 carbocyclic group, C3-C6 carbocyclic group, C3-C7 carbocyclic group, C3-C8 carbocyclic group, C3-C9 carbocyclic group, C3-C10 carbocyclic group, C3-C11 carbocyclic group, C3-C12 carbocyclic group, C3-C4 substituted carbocyclic group, C3-C5 substituted carbocyclic group, C3-C6 substituted carbocyclic group, C3-C7 substituted carbocyclic group, C3-C8 substituted carbocyclic group, C3-C9 substituted carbocyclic group, C3-C10 substituted carbocyclic group, C3-C11 substituted carbocyclic group, or C3-C12 substituted carbocyclic group, which has one or more carbon atoms substituted by hetero atoms. The heterocyclic group may also be a C4-C7 carbocyclic group or C4-C7 substituted carbocyclic group, which has one or more carbon atoms substituted with hetero atoms. The examples of heterocyclic groups may be a thienyl group, pyrrolyl group, furyl group, imidazolyl group, pyridyl group, or the like. The deletion site of the hydrogen may be any site which is chemically possible, and it may be on an aromatic ring or on a nonaromatic ring.

As used herein, "phenyl group" refers to a C6 aromatic carbocyclic group and is a functional group lacking one H from benzene. "Substituted phenyl group" refers to a group in which H in a phenyl group is substituted with a substituent as defined below.

As used herein, carbocyclic group or heterocyclic group may be substituted by a bivalent substituent in addition to being able to be substituted by a monovalent substituent as defined below. Such a bivalent substitution may be oxo substitution (=O) or thioxo substitution (=S).

As used herein, "halogen" refers to a monovalent group of elements such as fluorine (F), chlorine (Cl), bromine (Br), iodine (I) and the like which belong to group 7B of the periodic table.

As used herein, "hydroxy" refers to a group represented by —OH. The term "substituted hydroxy" refers to hydroxy having the H of the hydroxy substituted by a substituent as defined below.

As used herein, "cyano" refers to a group represented by —CN, and "nitro" refers to a group represented by —NO$_2$. The term "amino" refers to a group represented by —NH$_2$. The term "substituted amino" refers to amino having an H substituted by a substituent defined below.

As used herein, "carboxy" refers to a group represented by —COOH. The term "substituted carboxy" is carboxy having an H substituted by a substituent as defined below.

As used herein, "thiocarboxy" refers to a group having an oxygen atom of carboxy group substituted with a sulfur atom, and can be represented by —C(=S)OH, —C(=O)SH or —CSSH. The term "substituted thiocarboxy" is thiocarboxy having the H substituted by a substituent as defined below.

As used herein, "acyl" refers to alkylcarbonyl containing the "alkyl" bound to carbonyl, cycloalkylcarbonyl containing the "cycloalkyl" bound to carbonyl, and arylcarbonyl containing the "aryl" bound to carbonyl. "Acyl" refers to, for example, acetyl, n-propanoyl, i-propanoyl, n-butyloyl, t-butyloyl, cyclopropanoyl, cyclobutanoyl, cyclopentanoyl, cyclohexanoyl, benzoyl, α-naphthoyl, and β-naphthoyl. "Substituted acyl" refers to acyl having hydrogen substituted with a substituent as defined below.

As used herein, "amido" refers to a group having a hydrogen of ammonia substituted with an acid group (acyl group), and, preferably, represented by —CONH$_2$. The term "substituted amido" refers to amido which is substituted.

As used herein, "carbonyl" refers to a generic term for a substance including —(C=O)—, which is a characteristic group of aldehydes and ketones. The term "substituted carbonyl" refers to a carbonyl group substituted by a substituent selected as described below.

As used herein, "thiocarbonyl" refers to a group having the oxygen atom of carbonyl substituted by a sulfur atom, and includes a characteristic group —(C=S)—. The thiocarbonyl includes thioketone and thioaldehyde. The term "substituted thiocarbonyl" refers to a thiocarbonyl substituted by a substituent selected as described below.

As used herein, "sulfonyl" is a generic term for a substance including a characteristic group, —SO$_2$—. The term "substituted sulfonyl" refers to a sulfonyl substituted by a substituent selected as described below.

As used herein, "sulfinyl" is a generic term for a substance including a characteristic group, —SO—. The term "substituted sulfinyl" refers to a sulfinyl substituted by a substituent selected as described below.

As used herein, "aryl" refers to a group generated when one hydrogen atom linked to a ring of aromatic hydrocarbons is eliminated, and included in a carbocyclic group in the present specification. Examples thereof include phenyl, α-naphthyl, β-naphthyl, anthyl, indenyl, phenanthryl and the like. "Substituted aryl" refers to an aryl substituted with a substituent selected as described below.

As used herein, "heteroaryl" refers to a group generated when one hydrogen atom linked to a ring of aromatic hydrocarbons having hetero atoms is eliminated, and included in a "heterocyclic group" in the present specification. Examples thereof include furanyl, thiophenyl, pyridyl and the like. "Substituted heteroaryl" refers to a heteroaryl substituted with a substituent selected as described below.

As used herein, "ester" refers to a generic term for a substance including —COO—, which is a characteristic group. The term "substituted ester" refers to ester substituted with a substituent selected as describe below.

As used herein, "hydroxyl group" refers to a group represented by —OH. "Hydroxyl group" is interchangeable with "hydroxyl group".

As used herein, "alcohol" refers to an organic compound having one or more hydrogen atoms of an aliphatic hydrocarbon substituted by a hydroxyl group and may be used interchangeably with "alcohol derivative". It is also represented as ROH in the present specification. Herein, R is an alkyl group. Preferably, R may be C1-C6 alkyl. Alcohol may be, for example, methanol, ethanol, 1-propanol, 2-propanol and the like, but is not limited to these.

As used herein, "aldehyde" refers to a generic term for a substance including —CHO, which is a characteristic group. "Substituted aldehyde" refers to an aldehyde substituted with a substituent selected as described below, and may be used interchangeably with "aldehyde derivative".

As used herein, "amine" is a general name for compounds obtained by substituting hydrogen atom of ammonia $NH_3$ with a hydrocarbon group and classified into a primary amine, a secondary amine, and a tertiary amine depending on the number of the hydrocarbon groups. The term "amine" in this specification is used interchangeably with "amines".

As used herein, "carboxylic acid" refers to a generic term for a substance including —COOH, which is a characteristic group, and are interchangeable with "carboxylic acid". "Substituted carboxylic acid" refers to a carboxylic acid substituted with a substituent selected as described below, and may be used interchangeably with "aldehyde derivative".

As used herein, "amino acid" may be a natural or non-natural amino acid. "Amino acid derivative" or "amino acid analogue" refers to those which are different from naturally occurring amino acids but have the same functions as those of the original amino acids. Such amino acid derivatives and amino acid analogous are well known in the art. The term "natural amino acid" or "naturally occurring amino acid" refers to the L-isomer of a natural amino acid. Examples of the natural amino acid include glycine, alanine, valine, leucine, isoleucine, serine, methionine, theronine, phenylalanine, tyrosine, tryptophane, cysteine, proline, histidine, aspartic acid, asparagine, glutamic acid, glutamine, γ-carboxyglutamic acid, arginine, ornithine, and lysine. As used herein, unless otherwise specified, all amino acids are L-stereoisomer, however a embodiment using D-amino acid is also included in the invention. The term "non-natural amino acid" or "non-naturally occurring amino acid" refers to an amino acid which generally can not be found in a protein. Examples of the non-natural amino acid include D-isomers and L-isomers of norleucine, p-nitrophenylalanine, homophenylalanine, p-fluorophenylalanine, 3-amino-2-benzylepropionic acid, and homoarginine and D-phenylalanine. "Amino acid analogue" refers to a molecule which is not an amino acid but has an analogous physical property and/or function to an amino acid. Examples of the amino acid analogue include ethionine, canavanine, and 2-methylglutamine. Amino acid mimetics refer to compounds which have different chemical structures from amino acids but render functions in the same manner as naturally occurring amino acids. As used herein, "amino acid" may be protected with a protecting group.

As used herein, "alkylbenzene" refers to an alkyl derivative of benzene, that is, an aromatic hydrocarbon in which an alkyl group is bonded to the benzene nucleus and the term is used interchangeably with the term "alkylbenzenes" in this specification. The term "alkyl group" is the above defined "alkyl".

As used herein, "terpene" refers to a hydrocarbon having a composition of $(C_5H_8)_n$, and this term also includes oxygen-containing compounds which are derived from the hydrocarbon and have different degree of unsaturation from the hydrocarbon. The term "terepene" is used interchangeably with the term "terepenes" in this specification.

As used herein, "ether" refer to a compound defined by the general formula, A-O-A' wherein a group for A and a group for A' may be same or different and may independently denote a group selected from alkyl, substituted alkyl, cycloalkyl, substituted cycloalkyl, cycloalkenyl, substituted cycloalkenyl, carbocyclic, substituted carbocyclic and the like, as defined above. Also, the group for A and the group for A' may be bonded to each other to form a cyclic ether. The term "ether" is used interchangeably with the term "ethers" in this specification.

As used herein, "silane" is a generic name for silicon hydrides and in accordance with the number of silicon, there are monosilane, disilane, and trisilane. The term "silane" is used interchangeably with the term "silanes".

As used herein, "thiol" is a group (mercapto group) obtained by substituting oxygen atom of hydroxyl group with sulfur atom, and expressed as —SH. As used herein, the term "thiol" and "thiols" are used interchangeably. "Substituted thiol" refers to a mercapto group of which hydrogen atom (H) is substituted with the following substituents.

As used herein, C1, C2, . . . Cn indicate the number of carbon atoms. Accordingly, C1 is used for expressing a substituent having one carbon atom.

As used herein, "optical isomer(s)" refers to a pair of compounds or one of the compounds, whose crystalline or molecular structures are mirror images and non-superimposable. It also refers to one of stereoisomers, wherein a set of the optical isomers share the same properties except the optical activity.

As used herein, "substitution" refers to substituting one or two or more hydrogen atom(s) in an organic compound or a substituent with another atom or atomic group, if not particularly mentioned. It is possible to remove one hydrogen atom to substitute with a monovalent substituent, and to remove two hydrogen atoms to substitute with bivalent substituent.

As used herein, examples of the substituent include, but not limited to, alkyl, cycloalkyl, alkenyl, cycloalkenyl, alkinyl, alkoxy, a carbocyclic group, a heterocyclic group, halogen, hydroxy, thiol, cyano, nitro, amino, a carboxy group, carbamoyl, acyl, acylamino, thiocarboxy, substituted amido, substituted carbonyl, substituted thiocarbonyl, substituted sulfonyl, and substituted sulfinyl.

As used herein, "protection reaction" refers to a reaction to add a protecting group such as t-butoxycarbonyl group to a functional group which is desired to be protected. By protecting a functional group with a protecting group, the reaction of a functional group having high reactivity can be suppressed, and only a functional group having lower reactivity reacts.

As used herein, "deprotection reaction" refers to a reaction to eliminate a protecting group such as t-butoxycarbonyl. The deprotection reaction may be a reaction such as a reaction using trifluoroacetic acid (TFA) or a reduction reaction using Pd/C.

In the respective methods of the present invention, intended products may be isolated by removing foreign substances (unreacted raw material, by-product, solvent and the like) from a reaction solution using a method commonly used in the art (for example, extraction, distillation, washing, concentration, precipitation, filtration, drying or the like), and then combining after-treatment methods commonly used in the field of the art (for example, adsorption, dissolution, elution, distillation, precipitation, deposition, chromatography, or the like).

DESCRIPTION OF PREFERRED EMBODIMENTS OF THE INVENTION

Hereinafter, a preferable embodiment of the invention will be described.

In one aspect, the invention provides a method for separating, concentrating, or refining a carbon nanotube having a desired physical property in a sample, wherein the method comprises steps: a) irradiating light to a sample containing a carbon nanotube; and b) selecting the carbon nanotube having a desired physical property. So far, the conventional methods for producing carbon nanotubes has produced carbon nanotubes which contain various carbon-containing contaminants, and do not have uniformity in diameter and chiral vector. In the above-mentioned step a), the light is radiated under conditions (e.g., the light intensity, the distance between a sample and a light source, and the light irradiation time) sufficient to induce the photocatalytic reaction. In the above-mentioned step b), techniques are used for selecting, i.e., collecting or concentrating, a carbon nanotube having a desired physical property, for example, uniformity in at least either a diameter or a chiral vector, from a crude composition containing or expected to contain a carbon nanotube produced by a conventional method or a commercially available carbon nanotube or an organic solution, an aqueous solution or a water-based dispersion containing the crude composition. The method allows for the highly selective separation and purification of the carbon nanotubes which have theoretically possible a desired uniformity in at least either a diameter or a chiral vector, from a sample containing carbon nanotubes with a low purity in terms of the diameter and/or chiral vector thereof. The present method also allows separation of single-walled carbon nanotubes which have a desired physical property, that is, still higher uniformity in at least either a diameter or a chiral vector. The light used for the step a) has a specific wavelength within a range covering from the near infrared region to the ultraviolet region (typically, from around 300 nm to 4000 nm). More preferably, the light is monochromatic light or laser light, which has a specific wavelength within a range covering from the near infrared region to the ultraviolet region. Utilization of monochromatic light or laser light has an advantage in obtaining the narrower distribution or the uniformity of at least either a diameter or a chiral vector of the obtained carbon nanotubes.

In a preferable embodiment, the light irradiation in the step a) is carried out in the presence of a metal. The metal may be a metal catalyst used during the production of the carbon nanotubes before the separation. Alternatively, carbon nanotubes in the presence of a metal may be provided by removal of metals from commercially available carbon nanotubes, followed by addition of a predetermined metal to the nanotubes. Accordingly, light irradiation in the step a) of the above-mentioned method may selectively induce photocatalytic reactions and deposition such as electrodeposition of the metal on a targeted carbon nanotube in the solution. In the above process, selection of the radiated light wavelength and the type of metal to be deposited or electrodeposited on the excited carbon nanotubes by the irradiation, can allow the selectivity in the diameter and the chiral vector of the carbon nanotubes, and in the absolute potential at von Hove Singularity (vHs) of the carbon nanotubes. A metal used in the invention may be selected from the group consisting of alkali metals; alkaline earth metals; transition metals selected from Group IIIA to VIIA elements and Group IB elements; and rare earth elements. A typical example of the metals used in the invention may include, but not limited to, Fe, Ni, Cu, Ag, Co or Mn. The metal used in the invention can be selected properly depending the positional relationship between the redox potential of the metal and the electronic energy level of carbon nanotubes (particularly, the single-walled carbon nanotube). According to the invention, in considering that the larger the overlap of energy levels between the redox potential of the metal and the electronic energy levels of the carbon nanotube in the solution, the more likely the metal has deposited on the carbon nanotube; a metal which has a larger overlap in energy levels with the desired carbon nanotubes can be selected under the specific distribution of the energy levels in the solution.

In one preferable embodiment, the selection of the carbon nanotube in the step b) is carried out by applying a predetermined magnetic field so as to collect the carbon nanotube having a desired physical property (including at least either a diameter or a chiral vector). Application of such a magnetic field provides collection or concentration of the carbon nanotube on which the metal is deposited.

In another preferable embodiment, the selection of the carbon nanotube in the step b) is carried out by a common chromatography technique.

As described, the selection of the carbon nanotube in the step b) may be carried out by application of the magnetic field or chromatographic technique.

In a further preferred embodiment, in the invention, the method for separating, concentrating, or purifying the carbon nanotube having a desired physical property (including at least either a diameter or a chiral vector) in a sample is carried out using a dispersion or a solution of the carbon nanotube. At the time of producing the dispersion of the carbon nanotubes, a surfactant can be added to the sample containing the carbon nanotubes. Exemplary examples of the surfactant used in the invention are selected from, but not limited to, the group consisting of sodium dodecyl sulfate, sodium dodecylbenzenesulfonate, Triton X (Triton X-100), alkylsulfonaic acid salt, sodium polyoxyethylene alkyl ether sulfate, benzalconium chloride, alkyltrimethylammonium chloride, benzyltrimethylammonium chloride, nonyl phenol ethoxylate, octyl phenyl polyoxyethylene ether, lauryl polyoxyethylene ether, and cetyl polyoxyethylene ether. Among them, sodium dodecyl sulfate, sodium dodecylbenzenesulfonate, and Triton X (Triton X-100) are particularly preferable. The concentration of the surfactant in the solution may be a concentration which is equal to or higher than the critical micellar concentration (cmc) of the surfactant used; and may be within a range allowing dispersion of the carbon nanotube as a micelle.

It is known that the carbon nanotubes consisting of pure carbon are not soluble in any solvent. However, in order to solubilize the carbon nanotubes in an organic or water-based solvent, the carbon nanotubes may be substituted with a suitable substituent. In order to solubilize the carbon nanotubes in water, it is preferable to surface-modify the carbon nanotubes of pure carbon with a saturated or unsaturated carbon chain molecule having a carboxyl group or an amino group as a substituent in the molecule through a covalent bond, an ionic bond, a hydrogen bond, or an intermolecular interaction.

In another preferable embodiment, in the present invention, a sample used for a method of separating, concentrating, or purifying the carbon nanotube having a desired physical property (at least either a diameter or a chiral vector) in the sample, is a solution further containing a metal ion and/or an electron donor. The concentration of the metal ion in the solution is preferably 0.001 to 10%, more preferably 0.05 to 5%, and even more preferably 0.1 to 1%. The concentration of the metal ion in the solution is lower than 0.001% is not preferable, because of insufficient deposition of the metal on the carbon nanotube surface. The concentration over 10% of the ions is not preferable, because it becomes difficult to carry out purification at the time of removing the metal impurity from the carbon nanotube thereafter. The concentration of the electron donor in the solution is preferably equal to or higher than that of the metal ion used together. A typical electron donor used in the invention may be selected from, but not limited to the group consisting of alcohols, amines, arginine, benzaldehyde, hydrazine, carboxylic acids, amino acids, toluene, alkylbenzenes, terepenes, ethers, silanes, and thiols. The electron donor in the invention is preferably alcohols and particularly preferably methanol.

In a preferable embodiment, the invention provides a method of analyzing the carbon nanotube having a desired physical property in a sample, including a method comprising the steps of a) irradiating light to a sample expected to contain the carbon nanotube; b) selecting the carbon nanotube having the desired physical property; and c) identifying the selected carbon nanotube.

The carbon nanotube having a desired physical property (including at least either a diameter or a chiral vector) is provided by the method of the invention described above. Also, a carbon nanotube composition with an increased content of the carbon nanotube having a desired physical property with a desired uniformity (including at least either a diameter or a chiral vector) is provided by the method of the invention described above. Further, a carbon nanotube composition containing the carbon nanotube having a high purity (greater than or equal to 99%) and having uniformity in diameter and chiral vector can be provided. These carbon nanotube compositions can be a carbon nanotube supply source useful for production of a carbon nanotube thin film contained in an optical filter or an electron device. A typical example of the electron device may include a conductive thin film, a dielectric thin film, a sensor electrode, an electrode for a high energy density fuel cell, a highly functional display, a single-molecule detection sensor, an acceleration detection sensor, and a magnetic field detection sensor.

The carbon nanotube obtained by the method of the invention may be adsorbed/fixed on a support or accumulated on a support to form a carbon nanotube thin film. Also, if the carbon nanotube is adsorbed and fixed in predefined patterns on a support, carbon nanotubes can be obtained in predefined patterns on a support.

In another aspect, the invention provides an apparatus for separating, concentrating, or purifying a carbon nanotube having a desired physical property in a sample and comprising A) an introduction part for a sample containing the carbon nanotube; B) means for irradiating light to the sample; and C) means for selecting the carbon nanotube having the desired physical property (including at least either a diameter or a chiral vector).

In a preferable embodiment, the means B) is a light source of monochromatic light or laser light having specific wavelength within a range covering from the near infrared region to the ultraviolet region so as to deposit a metal on the carbon nanotube. In the invention, as the means B), a polychromatic light source having certain wavelength within a range covering from the near infrared region to the ultraviolet region so as to deposit a metal on the carbon nanotube may be used (see FIG. 8).

In another preferable embodiment, the means C) may be an electromagnet with controllable magnetism for generating a predetermined magnetic field for integrating the carbon nanotube having a desired physical property (including at least either a diameter or a chiral vector) or chromatography.

In another preferable embodiment, the carbon nanotube is continuously supplied in the form of a dispersion by flowing a sample containing the carbon nanotube. Accordingly, the carbon nanotube is deposited selectively as similarly described above, resulting in a two to ten times increase in the amount of the deposition.

In still another embodiment of the invention, a similar experiment may be carried out by limiting the light irradiating portion of the light source with a lithographic pattern mask (e.g., 10 μm width). As a result, the carbon nanotube can be space-selectively deposited with the structure selectivity as similarly described above. Accordingly, the carbon nanotube having a specific chiral vector can be separated and purified and fixed at an optional position of a substrate.

In still another further embodiment of the invention, light irradiation is carried out by a near-field probe chip. In this case, the light irradiation time is controlled to be pulsed light (e.g., 10 ms), so that one carbon nanotube having a specific chiral vector can be space-selectively fixed on the substrate surface with the structure selectivity as similarly described above. Accordingly, the carbon nanotube having a specific chiral vector can be fixed on an optional position while the number of the carbon nanotube is controlled to be a single or another optional number.

The reference documents such as scientific documents, patents, and patent applications cited in this specification are hereby incorporated by reference in their entirety, as if they were literally described in this specification.

The above description illustrates preferred embodiments that achieve the features and advantages of the invention; however the invention should not be construed to be limited to the illustrated embodiments. It is understood that the scope of the invention should be construed only by claims. It should be understood that the person skilled in the field can conduct the inventions according to the practically described preferred embodiments of the inventions based on the technical common knowledge and skills. Also, it should be understood that the reference documents cited in this specification are hereby incorporated by reference in their entirety, as if they were literally described in this specification.

EXAMPLES

Hereinafter, the invention will be described more in detail along with examples, however it is not intended that the invention be limited to the illustrated examples.

Example 1

1.1 Metal Deposition on a Carbon Nanotube

Carbon nanotubes (CarboLex AP-Grade SWNT (SWNT: purity 50-70%)) in an aqueous 1% sodium dodecyl sulfate (SDS) solution were subjected to ultrasonic dispersion treatment at 24° C. and 12000 rpm for 15 minutes and the supernatant solution was filtered with a syringe filter (0.2 μm pore size filter) and subjected to additional ultrasonic treatment and centrifugal separation in the same conditions to obtain a micellar dispersion.

Next, methanol (Methanol: 99.8% purity, Infinity Pure Grade; commercially available from Wako Pure Chemical Industries, Ltd.) was added as an electron donor to the dispersion to a concentration of 0.1%. The following three different metal ion solutions were added to the above resulting solution to prepare three solutions with different metal ions.

Figure 4:
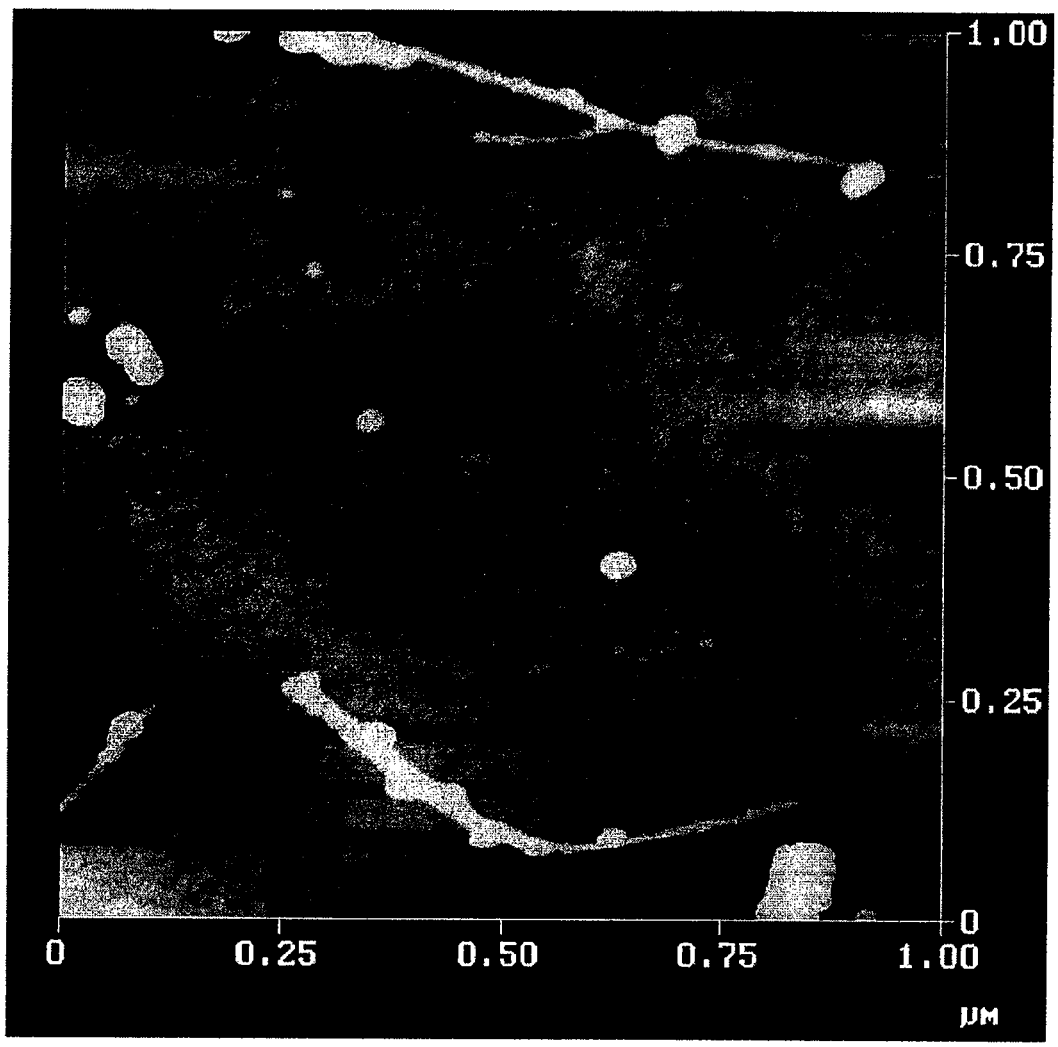
FIG. 4 shows an atomic force microscopic image of the carbon nanotube surface in which a metal is deposited.

I) 0.1 M Fe(NH$_4$)$_2$(SO$_4$)$_2$ aqueous solution
II) 0.1 M CoCl$_2$ aqueous solution
III) 0.1 M MnCl$_2$ aqueous solution Monochromatic light with an excitation wavelength of 785 nm was simultaneously radiated under the same conditions to the three solutions produced in the above-mentioned manner for excitation. Ions of the metals (Mn, Co, and Fe) in the solutions were respectively reduced and deposited on the specific carbon nanotubes. The surface of the carbon nanotube on which each metal was deposited, was observed by an atom-field microscope (AFM) (FIG. 4). For the measurement with AFM, NanoScope Multi Mode™ AFM manufactured by Digital Instruments was used in a tapping mode for the measurement, and NanoScope IIIa was used for analysis of the results. After each substrate on which the carbon nanotube was collected was carefully washed with ultra pure water (MilliQ water) and dried, the measurement was carried out in atmospheric air. From FIG. 4, it is made clear that each metal was electrodeposited on the surface of the carbon nanotube. The carbon nanotube on which the metal was deposited was collected by using a magnetic field (a magnet).

1.2 Raman Spectroscopy of Carbon Nanotube

Figure 5:
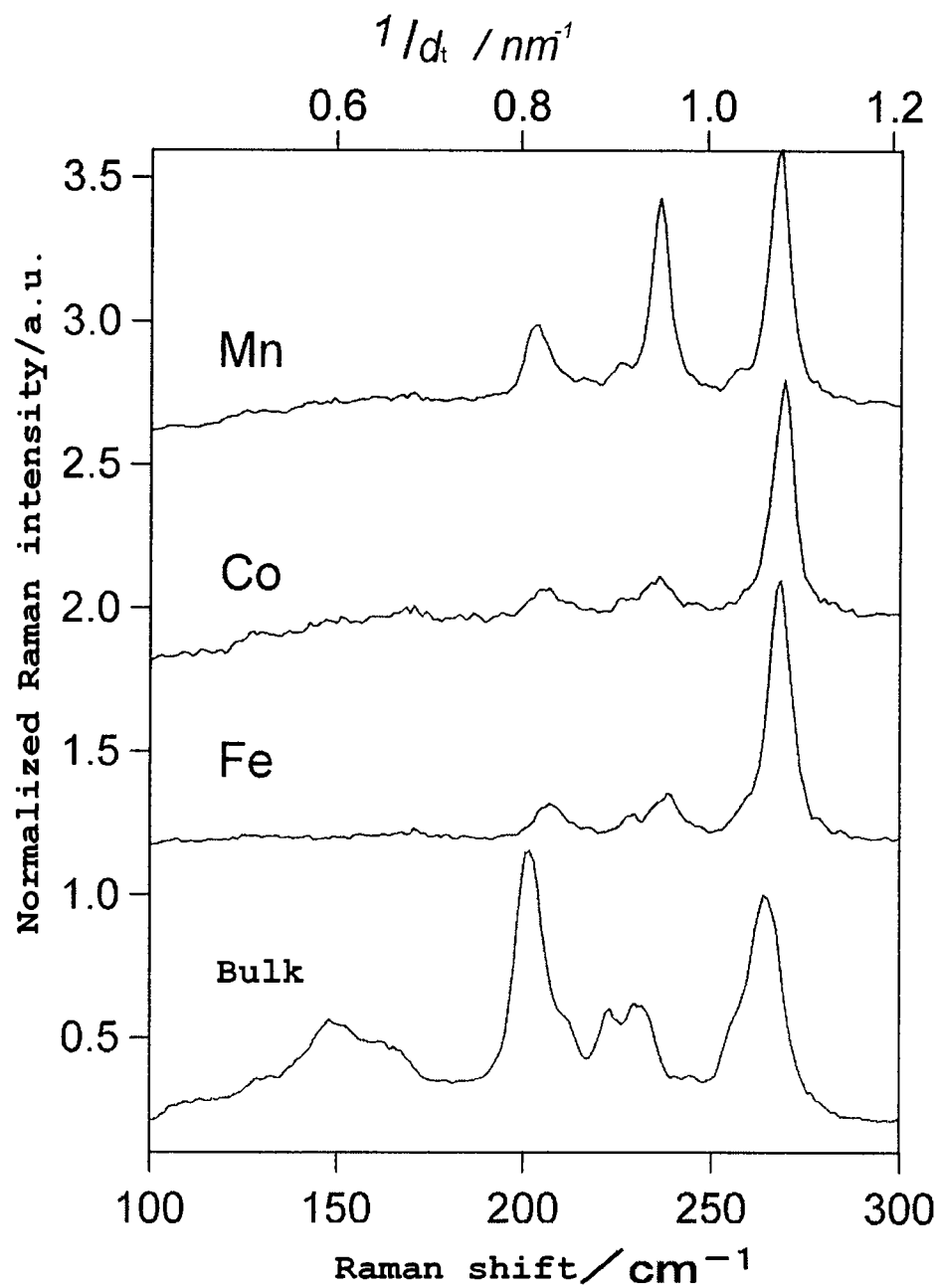
FIG. 5 shows Raman spectra in Radical Breathing Mode of the carbon nanotube before and after metal deposition in the invention.
Figure 6:
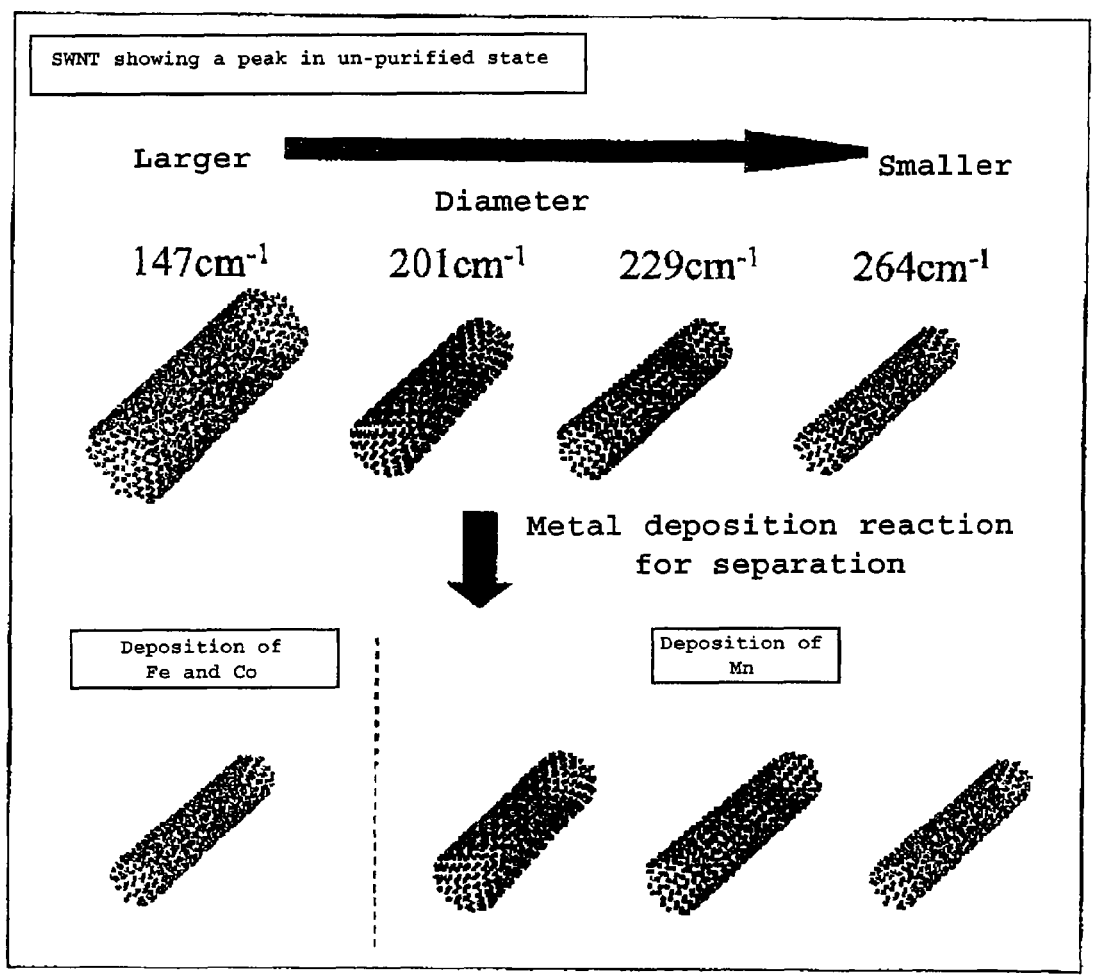
FIG. 6 shows the relation between the types of metals used in the invention and the diameter of a separated carbon nanotube.

The structure of each carbon nanotube collected in the above Section 1.1 was evaluated by a microscopic Raman measurement. FIG. 5 shows Raman spectra of the carbon nanotube before and after the deposition reaction of the metals in radial breaching mode. The spectra show the change of the shape having a plurality of peaks within a range of 140 to 270 cm$^{-1}$ to a shape having a main peak of 267 cm$^{-1}$ by the separation operation. It shows that only a semiconducting carbon nanotube having a diameter around 0.93 nm and chiral vector (10, 3) was selectively separated and recovered from the un-purified carbon nanotube sample having a wide diameter distribution with a diameter of 0.9 to 1.7 nm. Also, it is found that the spectra after the separation are changed depending on the deposited metals and it implies controllability of the separation by changing the types of metals in this exemplified method. The relation of the types of the metals used and the diameter of the separated carbon nanotube is shown in FIG. 6.

Figure 7:
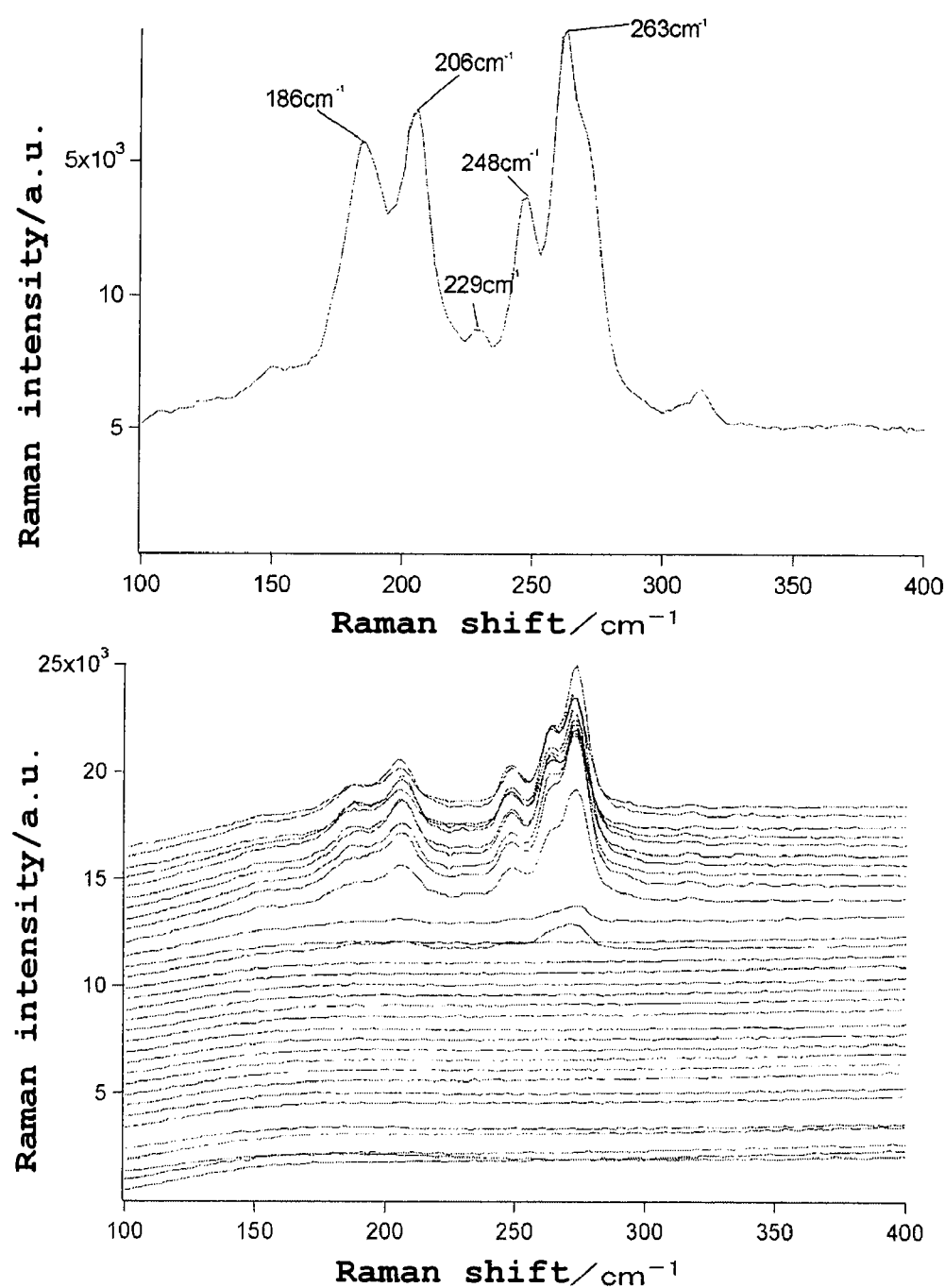
FIG. 7 shows the results of Fe ion deposition by excitation at 514 nm excitation wavelength.

FIG. 7 shows the result of the Fe ion deposition by excitation with an excitation wavelength of 514 nm. The result also shows that only the metallic carbon nanotube with a diameter around 0.90 nm and chiral vector (8, 5) was selectively separated and recovered from an un-purified carbon nanotube sample having a wide diameter distribution with a diameter of 0.9 to 1.7 nm.

Accordingly, it has been proved that the combination of a selective light-induced metal deposition reaction on a carbon nanotube with a magnetic field separation can allow for the high selectivity in purification of the carbon nanotube having a specific diameter and chirality.

Example 2

Figure 8:
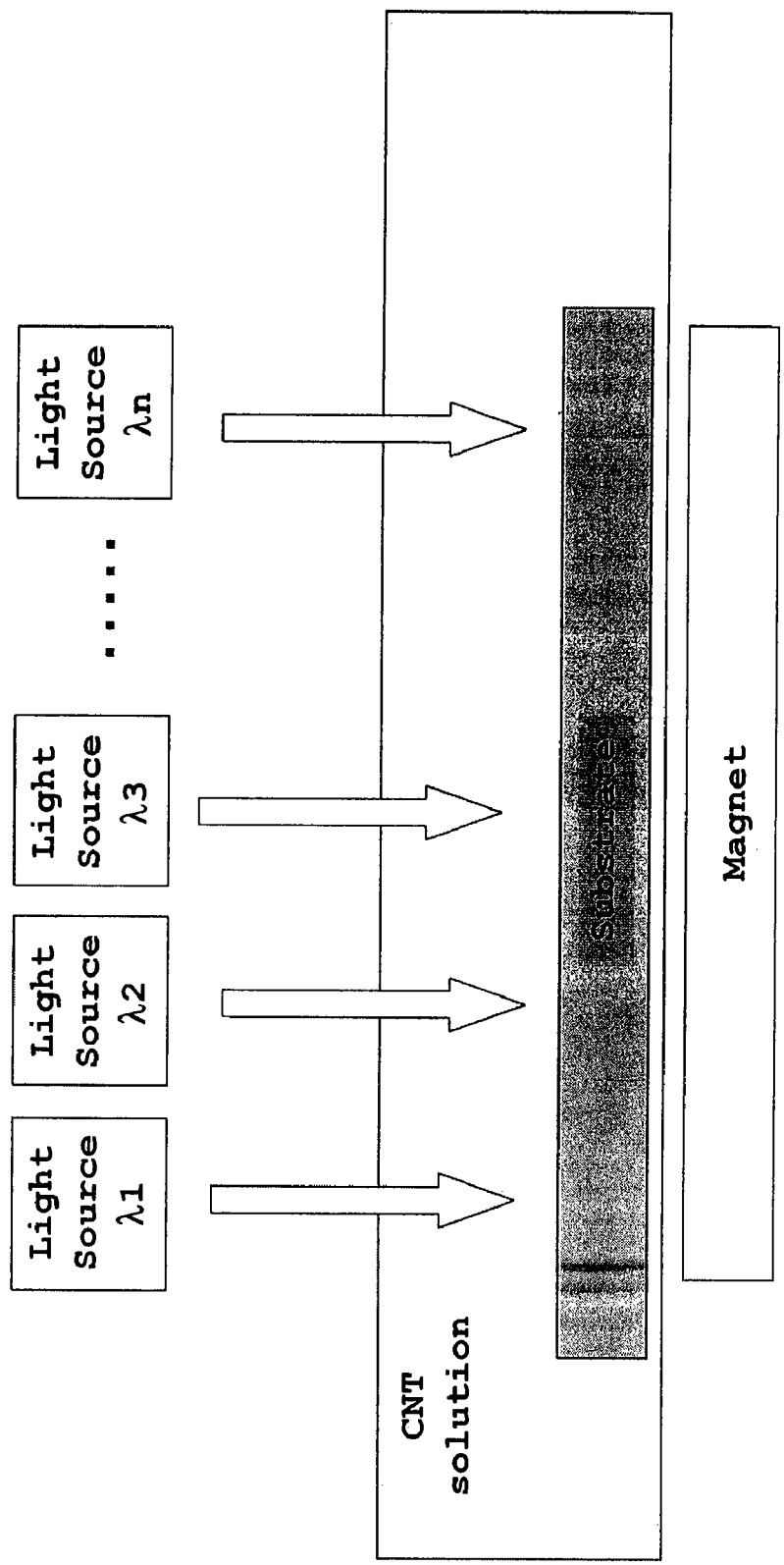
FIG. 8 shows the structural drawing of an apparatus of one embodiment of the invention.

FIG. 8 is an apparatus structural drawing showing one embodiment of the invention. Light with different wavelength values 1064 nm (λ1), 785 nm (λ2), and 514 nm (λ3) were employed as light irradiation sources for photoelectric chemical metal deposition. A micellar dispersion obtained by dispersing the carbon nanotube before purification in an aqueous 1% sodium dodecyl sulfate solution was used as the carbon nanotube-containing solution. A thin film glass was fixed in a reaction vessel and Fe(NH$_4$)$_2$(SO$_4$)$_2$ was added to the carbon nanotube-containing solution to a concentration of 0.1 M and light irradiation with the wavelength (λ1, λ2, or λ3) to the substrate was carried out for 10 minutes. After the carbon nanotube bearing the deposited metal was accumulated on the substrate, the carbon nanotube was washed with sulfuric acid and subjected to Raman spectroscopic measurement in the radial breathing mode to determine the chiral vector of the deposited carbon nanotube. In the portion to which the light irradiation with wavelength of λ1 was carried out, it was found that the carbon nanotube had the chiral vector (9, 1). Also, in the portion to which the light irradiation with wavelength of λ2 was carried out, it was found that the carbon nanotube having the chiral vector (11, 3) and (13,10) was collected, and in the portion to which the light irradiation with wavelength of λ3 was carried out, it was found that the carbon nanotube having the chiral vector (13, 1) was collected. Accordingly, the carbon nanotube having the specific chiral vector could be separated and purified.

TABLE 1

| | Chiral No. mettalic/ semiconducting | Band gap | Diameter | Raman shift |
|---|---|---|---|---|
| λ1 (1064 nm) | (9, 1)sc | 1.13 eV | 0.76 nm | 326.3 cm$^{-1}$ |
| λ2 (785 nm) | (11, 3)sc | 1.57 eV | 1.01 nm | 244.6 cm$^{-1}$ |
| | (13, 10)m | 1.58 eV | 1.59 nm | 156.4 cm$^{-1}$ |
| λ3 (514 nm) | (13, 1)sc | 1.17 eV | 1.07 nm | 231.8 cm$^{-1}$ |

Example 3

Figure 9:
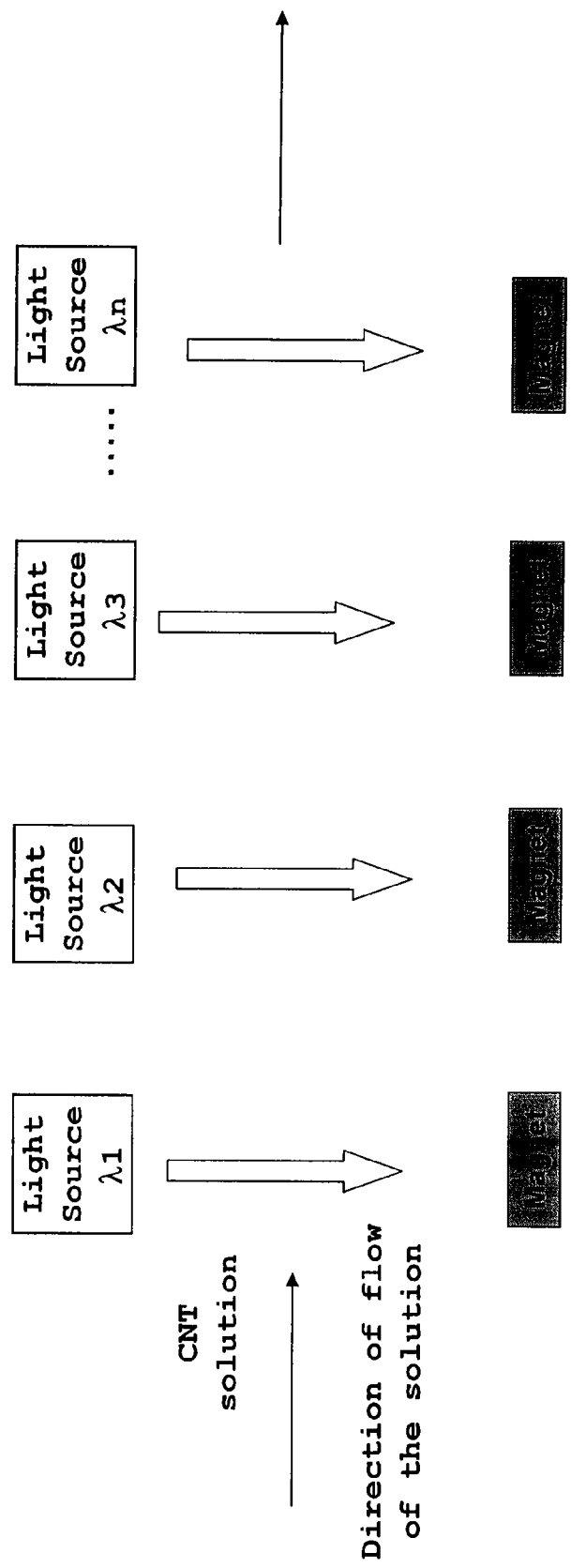
FIG. 9 shows the structural drawing of an apparatus of another embodiment of the invention.

FIG. 9 shows a drawing of an experiment carried out similar to that in the above-mentioned Example 2 with additional steps of flowing the carbon nanotube-containing solution and supplying the obtained carbon nanotube dispersion continuously. As a result, the carbon nanotube could be deposited selectively as similarly described above, resulting in a two to ten times increase in the amount of the deposition.

Example 4

Figure 10:
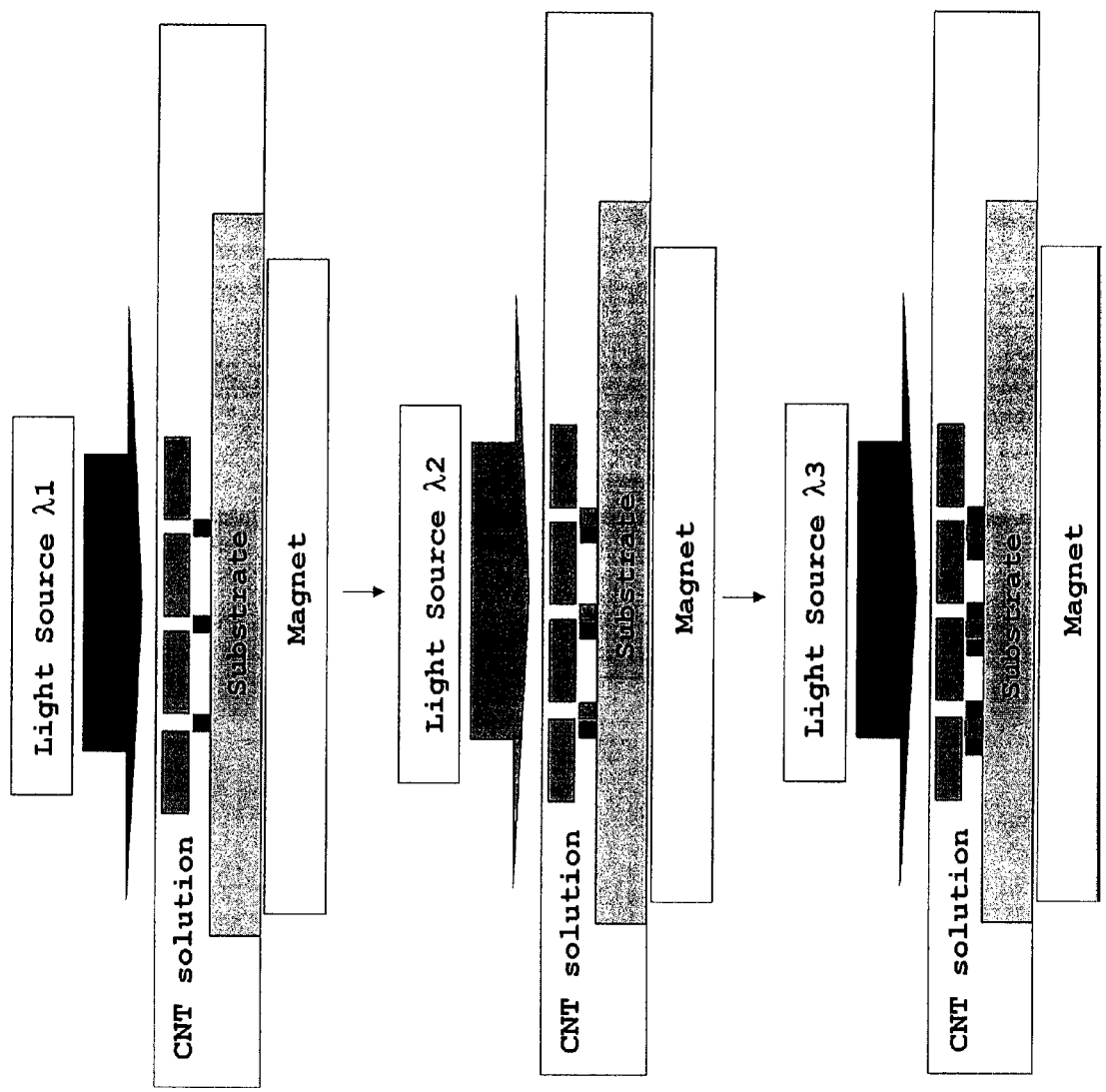
FIG. 10 shows the structural drawing of an apparatus of further another embodiment of the invention.

FIG. 10 shows a drawing of an experiment carried out similar to that in the above-mentioned Example 3, except that the light irradiation source was limited with a lithographic pattern mask (10 μm width). As a result, the carbon nanotube could be deposited space-selectively with the structure selectivity as described above. Accordingly, the carbon nanotube having the specific chiral vector could be separated, purified and fixed on any desired position of a substrate.

Figure 11:
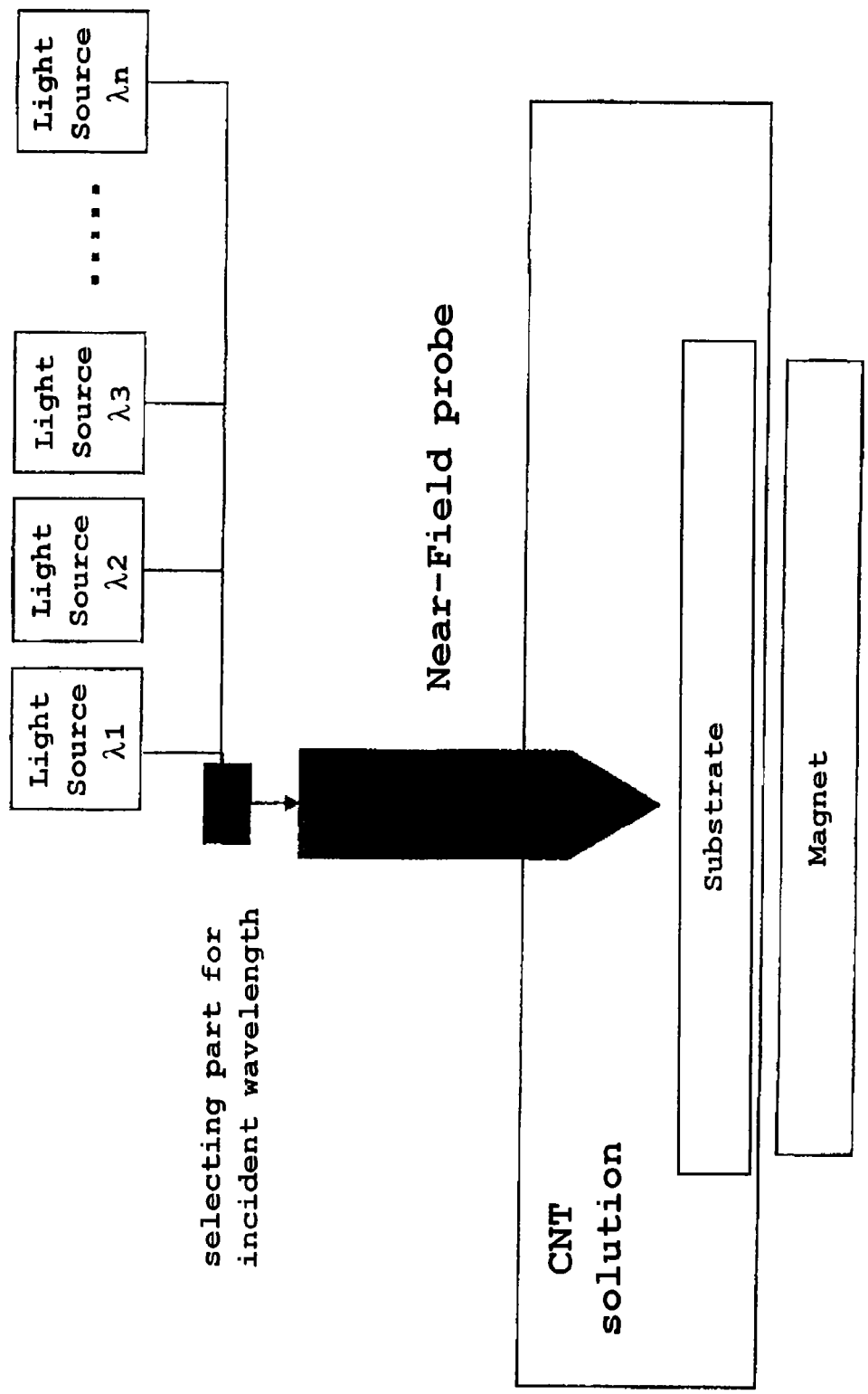
FIG. 11 shows the structural drawing of an apparatus of an even further another embodiment of the invention.

FIG. 11 shows a process drawing of an experiment carried out similar to that in the above-mentioned Example 2, except that a near-field probe chip for light irradiation was employed. In this case, a carbon nanotube was fixed position-selectively on a substrate surface with the chiral selectivity, in similar manner as described in Example 2, by setting the light irradiation time so as to provide the pulsed light (10 ms). Consequently, a single or an optionally controlled number of the carbon nanotubes having the specific chiral vector could be fixed at any position.

INDUSTRIAL APPLICABILITY OF THE INVENTION

According to the method and apparatus of the present invention, a carbon nanotube having an uniform desired physical property (including at least either a diameter or a chiral vector) can be highly selectively separated, concentrated, and purified by utilizing the characteristic structural susceptive of the carbon nanotube. Further, a thin film of the carbon nanotube with high purity separated by the above-mentioned method is useful as a next generation material for optical and electronic devices in the electronics and energy field.

The invention claimed is:

1. A method of separating, concentrating, or refining a carbon nanotube having a desired physical property from a sample solution, wherein the desired physical property includes at least one of a diameter or a chiral vector, the method comprising:
   a) irradiating light to the sample solution containing carbon nanotubes in the presence of metal ions, so that the metal ions are respectively reduced and deposited on the carbon nanotubes, and
   b) selecting the carbon nanotubes having the desired physical property by applying a predetermined magnetic field or chromatography to the carbon nanotubes so as to precipitate the carbon nanotubes with the desired physical property.

2. The method according to claim 1, wherein said carbon nanotube has a single-walled structure.

3. The method according to claim 1, wherein said light has a certain wavelength within a range covering from the near infrared region to the ultraviolet region.

4. The method according to claim 3, wherein said light is monochromatic light or laser light having said wavelength.

5. The method according to claim 1, wherein the metal ions are selected from the group consisting of alkali metals; alkaline earth metals; transition metals selected from the group consisting of Group IIIA to Group VIIA elements, Group VIII elements, and Group IB elements; and rare earth elements.

6. The method according to claim 1, wherein the step b) is carried out by applying a predetermined magnetic field to said carbon nanotube so as to precipitate the carbon nanotube with the desired physical property.

7. The method according to claim 1, wherein the step b) is carried out by chromatography.

8. The method according to claim 1, wherein said sample further contains a surfactant.

9. The method according to claim 8, wherein said surfactant is selected from the group consisting of sodium dodecyl sulfate, sodium dodecylbenzenesulfonate, Triton X, alkylsulfonates, sodium polyoxyethylene alkyl ether sulfate, benzalconium chloride, alkyltrimethylammonium chloride, benzyltrimethylammonium chloride, nonyl phenol ethoxylate, octyl phenyl polyoxyethylene ether, lauryl polyoxyethylene ether, and cetyl polyoxyethylene ether.

10. The method according to claim 1, wherein said sample is a water-based dispersion or an aqueous solution of the carbon nanotubes.

11. The method according to claim 1, wherein said carbon nanotubes are surface modified with a saturated or unsaturated carbon chain molecule having a carboxyl group or an amino group as a substituent in the molecule through a covalent bond, an ionic bond, a hydrogen bond, or an intermolecular interaction.

12. The method according to claim 1, wherein said sample solution further containing a metal ion and an electron donor.

13. The method according to claim 12, wherein said solution contains the metal ion at a concentration of 0.001 to 10%.

14. The method according to claim 12, wherein said solution contains the electron donor at a concentration of 0.001 to 10%.

15. The method according to claim 12, wherein said electron donor is selected from the group consisting of alcohols, amines, arginine, benzaldehyde, hydrazine, carboxylic acids, amino acids, toluene, alkylbenzenes, terpenes, ethers, silanes, and thiols.

* * * * *